US008399440B2

(12) United States Patent
Fogler et al.

(10) Patent No.: US 8,399,440 B2
(45) Date of Patent: Mar. 19, 2013

(54) DISEASE MODIFYING ANTI-ARTHRITIC ACTIVITY OF 2-METHOXYESTRADIOL

(75) Inventors: William E. Fogler, Rockville, MD (US); Stacy M. Plum, Arlington, VA (US); Carolyn F. Sidor, Chapel Hill, NC (US)

(73) Assignee: EntreMed, Inc., Rockville, MD (US)

( * ) Notice: Subject to any disclaimer, the term of this patent is extended or adjusted under 35 U.S.C. 154(b) by 905 days.

(21) Appl. No.: 11/726,361

(22) Filed: Mar. 20, 2007

(65) Prior Publication Data
US 2007/0231410 A1  Oct. 4, 2007

Related U.S. Application Data

(60) Provisional application No. 60/784,206, filed on Mar. 20, 2006.

(51) Int. Cl.
*A61K 31/56* (2006.01)
*A61K 31/497* (2006.01)

(52) U.S. Cl. .............. 514/171; 514/182; 514/252.1

(58) Field of Classification Search .............. 514/182, 514/252.02, 252.029, 252.1, 171
See application file for complete search history.

(56) References Cited

U.S. PATENT DOCUMENTS

| | | |
|---|---|---|
| 2,584,271 A | 2/1952 | Huffman |
| 2,846,453 A | 8/1958 | Hoehn |
| 3,117,140 A | 1/1964 | Heeker |
| 3,166,577 A | 1/1965 | Ringold et al. |
| 3,410,879 A | 11/1968 | Smith et al. |
| 3,470,218 A | 9/1969 | Farah |
| 3,492,321 A | 1/1970 | Crabbe |
| 3,496,272 A | 2/1970 | Kruger |
| 3,562,260 A | 2/1971 | De Ruggieri et al. |
| 3,956,348 A | 5/1976 | Hilscher |
| 4,172,132 A | 10/1979 | Draper et al. |
| 4,212,864 A | 7/1980 | Tax |
| 4,307,086 A | 12/1981 | Tax |
| 4,444,767 A | 4/1984 | Torelli et al. |
| 4,522,758 A | 6/1985 | Ward et al. |
| 4,552,758 A | 11/1985 | Murphy et al. |

(Continued)

FOREIGN PATENT DOCUMENTS

| | | |
|---|---|---|
| DE | 1907330 | 10/1969 |
| DE | 2 004 516 | 9/1970 |

(Continued)

OTHER PUBLICATIONS

Tishler et al., Ann Rheumat Dis, 1992;51(12):1330-1331.*

(Continued)

*Primary Examiner* — San-Ming Hui
(74) *Attorney, Agent, or Firm* — Suzannah K. Sundby, Esq.; Smith, Gambrell & Russell, LLP

(57) ABSTRACT

The present invention relates a composition for treating rheumatic diseases. The composition comprises a compound having the formula

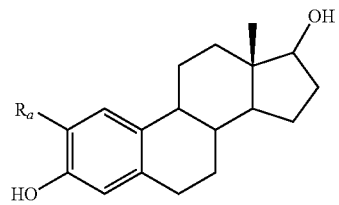

wherein $R_a$ is selected from $-OCH_3$, $-OCH_2CH_3$, $-CH_3$, $-CH_2CH_3$, $-CCCH_3$, $-CHCH-CH_3$, or $CH_2-CHCH_2$; and one or more anti-rheumatic agents. A method of using the composition for treating rheumatic diseases in humans and animals is also disclosed.

8 Claims, 8 Drawing Sheets

U.S. PATENT DOCUMENTS

| | | | |
|---|---|---|---|
| 4,634,705 A | | 1/1987 | DeBernardis et al. |
| 4,743,597 A | | 5/1988 | Javitt et al. |
| 4,808,402 A | | 2/1989 | Leibovich et al. |
| 4,994,443 A | | 2/1991 | Folkman et al. |
| 5,001,116 A | | 3/1991 | Folkman et al. |
| 5,135,919 A | | 8/1992 | Folkman et al. |
| 5,166,149 A | * | 11/1992 | Loev ............................ 514/186 |
| 5,252,718 A | | 10/1993 | Baird et al. |
| 5,504,074 A | | 4/1996 | D'Amato et al. |
| 5,521,168 A | | 5/1996 | Clark |
| 5,621,124 A | | 4/1997 | Seilz et al. |
| 5,629,327 A | | 5/1997 | D'Amato |
| 5,629,340 A | | 5/1997 | Kuwano et al. |
| 5,639,725 A | | 6/1997 | O'Reilly et al. |
| 5,643,900 A | * | 7/1997 | Fotsis et al. .................. 514/182 |
| 5,646,136 A | | 7/1997 | Petrow |
| 5,661,143 A | | 8/1997 | D'Amato et al. |
| 5,716,981 A | | 2/1998 | Hunter et al. |
| 5,733,876 A | | 3/1998 | O'Reilly et al. |
| 5,763,432 A | | 6/1998 | Tanabe et al. |
| 5,776,704 A | | 7/1998 | O'Reilly et al. |
| 5,792,845 A | | 8/1998 | O'Reilly et al. |
| 5,837,682 A | | 11/1998 | O'Reilly |
| 5,854,205 A | | 12/1998 | O'Reilly et al. |
| 5,854,221 A | | 12/1998 | Cao et al. |
| 5,861,372 A | | 1/1999 | Folkman et al. |
| 5,885,795 A | | 3/1999 | O'Reilly et al. |
| 5,892,069 A | | 4/1999 | D'Amato et al. |
| 5,919,459 A | | 7/1999 | Nacy et al. |
| 5,958,892 A | | 9/1999 | Mukhopadhyay et al. |
| 5,962,445 A | | 10/1999 | Stewart |
| 6,011,023 A | | 1/2000 | Clark et al. |
| 6,011,024 A | | 1/2000 | Reed et al. |
| 6,046,186 A | | 4/2000 | Tanabe et al. |
| 6,051,726 A | | 4/2000 | Sachdeva et al. |
| 6,054,598 A | | 4/2000 | Sachdeva et al. |
| 6,136,992 A | | 10/2000 | Ram et al. |
| 6,200,966 B1 | | 3/2001 | Stewart |
| 6,239,123 B1 | | 5/2001 | Green |
| 6,284,789 B1 | | 9/2001 | LaLonde et al. |
| 6,346,510 B1 | | 2/2002 | O'Reilly et al. |
| 6,358,940 B1 | | 3/2002 | Conney |
| 6,399,773 B1 | | 6/2002 | Liu et al. |
| 6,407,086 B2 | | 6/2002 | Faarup et al. |
| 6,410,029 B1 | | 6/2002 | Mukhopadhyay et al. |
| 6,413,513 B1 | | 7/2002 | Holaday et al. |
| 6,448,419 B1 | | 9/2002 | Paaren et al. |
| 6,514,971 B1 | | 2/2003 | Thomas et al. |
| 6,528,676 B1 | | 3/2003 | D'Amato et al. |
| 6,593,321 B2 | | 7/2003 | Rao et al. |
| 6,605,622 B2 | | 8/2003 | Green et al. |
| 6,723,858 B2 | | 4/2004 | D'Amato et al. |
| 6,730,665 B1 | | 5/2004 | Maran et al. |
| 6,759,386 B2 | | 7/2004 | Franco |
| 6,852,710 B2 | | 2/2005 | Rao et al. |
| 6,908,910 B2 | | 6/2005 | D'Amato et al. |
| 6,930,128 B2 | | 8/2005 | D'Amato et al. |
| 6,953,785 B2 | | 10/2005 | Ino et al. |
| 6,995,278 B2 | | 2/2006 | Agoston et al. |
| 6,998,395 B2 | | 2/2006 | Jackson et al. |
| 7,012,070 B2 | | 3/2006 | D'Amato et al. |
| 7,081,477 B2 | | 7/2006 | D'Amato et al. |
| 7,087,592 B1 | | 8/2006 | Agoston |
| 7,109,187 B2 | | 9/2006 | D'Amato et al. |
| 7,135,581 B2 | | 11/2006 | Agoston et al. |
| 7,291,610 B2 | | 11/2007 | D'Amato et al. |
| 7,351,729 B2 | | 4/2008 | Stein et al. |
| 7,371,741 B2 | | 5/2008 | Agoston et al. |
| 7,381,848 B2 | | 6/2008 | D'Amato et al. |
| 2002/0002294 A1 | | 1/2002 | D'Amato et al. |
| 2002/0035098 A1 | | 3/2002 | Slaga et al. |
| 2002/0068724 A1 | | 6/2002 | Slaga et al. |
| 2003/0027803 A1 | | 2/2003 | Slaga et al. |
| 2003/0036539 A1 | | 2/2003 | Slaga et al. |
| 2003/0073674 A1 | | 4/2003 | Slaga et al. |
| 2003/0096799 A1 | | 5/2003 | Rao et al. |
| 2003/0175961 A1 | | 9/2003 | Herron |
| 2004/0053906 A1 | | 3/2004 | Slaga et al. |
| 2004/0082558 A1 | 4/2004 | Tofovic et al. |
| 2004/0116397 A1 | 6/2004 | Slaga et al. |
| 2004/0121968 A1 | 6/2004 | Ljubimov |
| 2004/0156854 A1 | 8/2004 | Mulligan et al. |
| 2004/0186086 A1 | 9/2004 | Bunschoten et al. |
| 2004/0198671 A1 | 10/2004 | Bunschoten et al. |
| 2004/0209855 A1 | 10/2004 | Tofovic et al. |
| 2004/0214807 A1 | 10/2004 | D'Amato et al. |
| 2005/0014737 A1 | 1/2005 | Agoston et al. |
| 2005/0032766 A1 | 2/2005 | Green et al. |
| 2005/0070488 A1 | 3/2005 | Coelingh Bennik et al. |
| 2005/0101573 A1 | 5/2005 | Faarup et al. |
| 2005/0148565 A1 | 7/2005 | Cooperwood |
| 2005/0182038 A1 | 8/2005 | Cooperwood |
| 2005/0192258 A1 | 9/2005 | Agoston et al. |
| 2005/0203075 A1 | 9/2005 | Agoston |
| 2005/0250751 A1 | 11/2005 | Lee et al. |
| 2005/0266067 A1 | 12/2005 | Sengupta et al. |
| 2006/0025393 A1 | 2/2006 | Liao et al. |
| 2006/0025619 A1 | 2/2006 | Agoston et al. |
| 2006/0079576 A1 | 4/2006 | D'Amato |
| 2006/0116360 A1 | 6/2006 | Fogler |
| 2006/0135796 A1 | 6/2006 | Agoston |
| 2007/0135400 A1 | 6/2007 | Agoston et al. |
| 2007/0185069 A1 | 8/2007 | Plum et al. |

FOREIGN PATENT DOCUMENTS

| | | |
|---|---|---|
| DE | 27 57 157 | 12/1977 |
| DE | 3625315 | 1/1988 |
| EP | 0166937 A2 | 8/1986 |
| EP | 0281822 A2 | 9/1988 |
| EP | 0657175 A2 | 6/1995 |
| GB | 857080 | 12/1960 |
| GB | 857081 | 12/1960 |
| GB | 1570597 | 7/1980 |
| GB | 2252498 A | 8/1992 |
| JP | 39-5480 B | 0/0000 |
| JP | 41 000100 A | 1/1966 |
| JP | 42000928 B | 1/1967 |
| JP | 62-135472 | 6/1987 |
| JP | 63090763 A | 4/1988 |
| JP | 63-119500 | 5/1988 |
| JP | 04-046120 | 2/1992 |
| WO | WO 87/02367 A3 | 4/1987 |
| WO | WO 88/03151 A2 | 5/1988 |
| WO | WO 88/08002 A1 | 10/1988 |
| WO | WO 90/15816 A1 | 12/1990 |
| WO | WO 93/03729 A1 | 3/1993 |
| WO | WO 93/10805 A1 | 6/1993 |
| WO | WO 93/19746 A1 | 10/1993 |
| WO | WO 94/21288 A1 | 9/1994 |
| WO | WO 95/04535 A1 | 2/1995 |
| WO | WO 98/32763 A1 | 7/1998 |
| WO | WO 98/40398 | 9/1998 |
| WO | WO 99/01142 A1 | 1/1999 |
| WO | WO 99/22728 A1 | 5/1999 |
| WO | WO 99/33858 A3 | 7/1999 |
| WO | WO 99/33859 A2 | 7/1999 |
| WO | WO 99/35150 A3 | 7/1999 |
| WO | WO 99/45018 A1 | 9/1999 |
| WO | WO 00/07576 A2 | 2/2000 |
| WO | WO 00/10552 A2 | 3/2000 |
| WO | WO 00/66095 A2 | 11/2000 |
| WO | WO 00/68246 A1 | 11/2000 |
| WO | WO 01/27132 A1 | 4/2001 |
| WO | WO 01/85755 A1 | 11/2001 |
| WO | WO 02/15910 A1 | 2/2002 |
| WO | WO 2004/074307 A1 | 9/2004 |
| WO | WO 2004/101595 A1 | 11/2004 |
| WO | WO 2005/089256 A2 | 9/2005 |
| WO | WO 2007/059111 A2 | 5/2007 |

OTHER PUBLICATIONS

Office Action cited in U.S. Appl. No. 10/789,471 mailed Aug. 18, 2009, *USPTO Office Action*, pp. 1-11.

Office Action cited in U.S. Appl. No. 11/599,997 mailed Dec. 8, 2008, *USPTO Office Action*, pp. 1-9.

EPO Search, Supplementary European Search Report—EP 05736385, *EPO Search Report*, pp. 1-4, Jun. 30, 2009.
Hecker, Erich, Neue Ostranabkommlinge mit verschiedenen Substituenten in 3-Stellung, *Chemische Berichte*, vol. 95 (4), pp. 977, Oct. 12, 1961.
Lieur et al., Careinogenicity of Catechol Estrogens in Syrian Hamsters, *Journal of Steroid Biochemistry*, vol. 24 (1), pp. 353-356, Jan. 1, 1986.
EPO Search, EPO Supplementary Search EP 07753617, *EPO Search Report*, pp. 1-7, Apr. 14, 2010.
Treston, A. et al., Antiarthritic Activity of 2-Methoxyestradiol (2ME2) in a Rat Adjuvant-Induced Model of Rheumatoid Arthritis, *Inflammation Research*, vol. 54 (2), pp. S127, Aug. 1, 2005.
Arbiser et al., The Antiangiogenic Agents TNP-470 and 2-Methoxyestradiol Inhibit the Growth of Angiosarcoma in Mice, *Journal of the Amercian Academy of Dermatology*, vol. June, Part 1, pp. 925-929, Jun. 1999.
Office Action cited in U.S. Appl. No. 11/800,045, *USPTO Office Action*, pp. 1-10, Oct. 2, 2008.
Office Action cited in U.S. Appl. No. 11/437,850, mailed Sep. 19, 2008, *USPTO Office Action*, pp. 1-7.
Office Action cited in U.S. Appl. No. 11/519,570 mailed Dec. 9, 2008, *USPTO Office Action*, pp. 1-12.
USPTO, Notice of Allowance of U.S. Appl. No. 11/077,977 mailed Oct. 30, 2008, *USPTO Notice of Allowance*, pp. 1-9.
Lilopristone/(1-[4-(Dimethylamino)phenyl]-17-hydroxy-17-(3-hydroxy-1-propenyl)estra-4,9-diene-3-one; AK 98734, *Dictionary of Drugs* (1990), *Dict. of Steroids* (1991), *Dict. of Org. Cmpds* (6th Ed) (1996), 1990.
(paragraphs 583-584), *The Merck Index 11th Edition*, pp. 88, 1989.
*Research Plus Catalog*, pp. 50-58, 1993.
News Article: Hoffman-La Roche Signs $70 Million Deal with Millenium on Genomics Technology, *Genetic Engineering News*, Apr. 15, 1994.
News Article: Advanced Drug Delivery Systems Peak Interest of Pharmaceutical & Biotech Firms, *Genetic Engineering News*, Apr. 15, 1994.
News Article: Nasal Spray for Treating Bleeding Disorders, *Genetic Engineering News*, Apr. 15, 1994.
2-Methoxyestradiol—An Orally Active Endogenous Inhibitor of Angiogenesis, *EntreMed Website Article*, pp. 1-10, Jul. 11, 2000.
Peripheral Ulcerative Keratitis (Marginal Keratolysis; Peripheral Rheumatoid Ulceration) *Merck Manual of Diagnosis and Therapy*, vol. Sec. 8, pp. Chapter 8 & 96, Jan. 1, 1995.
Aboulwafa et al., Synthesis and evaluation for uterotrophic and antiimplantation activities of 2-substituted estradiol derivatives *Steroids*, vol. 57, pp. 199-204, Apr. 1992.
Adams, E.F. et al., Steroidal regulation of oestradiol-17B dehydrogenase activity of the human breast cancer cell line MCF-7 (Chemical Abstracts Doc. No. 109:32325, 1988) *Journal of Endocrinology*, vol. 118 (1), pp. 149-154, Jul. 1988.
Aguayo et al., Angiogenesis in Acute and Chronic Leukemias and Myelodysplastic Syndrome *Blood*, vol. 96 (6), pp. 2240-2245, Sep. 15, 2000.
Aizu-Yokota et al., Natural Estrogens Induce Modulation of Microtubules in Chinese Hamster V79 Cells in Culture, *Cancer Research*, vol. 55, pp. 1863-1868, May 1, 1995.
Akova et al., Optic Disk Neovascularization in a Patient with Cytomegalovirus Retinitis Associated with Renal Transplantation, *Ocular Immunology and Inflammation*, vol. 8 (1), pp. 63-65, Mar. 1, 2000.
Algire, G.H. et al., Vascular reactions of normal and malignant tumors in vivo. I. Vascular reactions of mice to wounds and to normal and neoplastic transplants, *Journal of the National Cancer Institute*, vol. 6, pp. 73-85, Aug. 1945.
Aliev et al., 54929q Synthesis of cycloalkyl derivatives of dihydric phenols and their ethers, *Chemical Abstracts*, vol. 72, pp. 370, 1970.
Amant et al., 2-Methoxyestradiol strongly inhibits human uterine sarcomatous cell growth, *Gynecologic Oncology*, vol. 91, pp. 299-308, Jan. 2003.
Amorino et al., Enhancement of Radiation Effects In Vitro by the Estrogen Metabolite 2-Methoxyestradiol, *Radiation Research*, vol. 153, pp. 384-391, Jan. 1, 2000.

Anderson et al., Mutliple Myeloma: New Insights and Therapeutic Approaches, *Hematology*, pp. 147-165, Jan. 1, 2000.
Anstead et al., The Estradiol Pharmacophore: Ligand Structure-Estrogen Receptor Binding Affinity Relationships and a Model for the Receptor Binding Site, *Steroids*, vol. 62, pp. 268-303, 1997.
Armstrong et al., Detection of Vascular Endothelial Growth Factor and Tumor Necrosis Factor Alpha in Epiretinal Membranes of Proliferative Diabetic Retinopathy, Proliferative Vitreoretinopathy and Macular Pucker, *Ophthalmologica*, vol. 212 (6), pp. 410-414, Nov. 1, 1998.
Arnoldi et al., Sweet Isovanillyl Derivatives: Synthesis and Structure-Taste Relationships of Conformationally Restricted Analogs, *Journal of Agric. Food Chem*, vol. 46(10), pp. 4002-4010, 1998.
Attalla et al., 2-Methoxyestradiol Arrests Cells in Mitosis without Depolymerizing Tubulin, *Biochemical and Biophysical Research Communications*, vol. 228, pp. 467-473, 1996.
Attalla et al., 2-Methoxyestradiol-Induced Phosphorylation of Bcl-2: Uncoupling from JNK/SAPK Activation, *Biochemical and Biophysical Research Communications*, vol. 247 (3), pp. 616-619, Jun. 29, 1998.
Audier et al., Orientation de la fragmentation en spectrometrie de masse par introduction de groupements fonctionnels. VII.— Etheylenecetals de ceto-2 steroides, *Bulletin De La Societe Chimique De France*, vol. 10, pp. 3088-3090, 1965.
Avvakumov et al., Crystal Structure of Human Sex Hormone-binding Globulin in Complex with 2-Methoxyestradiol Reveals the Molecular Basis for High Affinity Interactions with C-2 Derivatives of Estradiol, *The Journal of Biological Chemistry*, vol. 277 (47), pp. 45219-45225, Nov. 22, 2002.
Ayala et al., The Induction of Accelerated Thymic Programmed Cell Death During Polymicrobial Sepsis: Control by Corticosteroids but not Tumor Necrosis Factor, *Shock*, vol. 3 (4), pp. 259-267, Apr. 1995.
Azuma, H., Genetic and Molecular Pathogenesis of Hereditary Hemorrhagic Telangiectasia, *Journal of Medical Investigation*, vol. 47 (3-4), pp. 81-90, Aug. 1, 2000.
Bacharach et al., In vivo Patterns of Expression of Urokinase and Its Inhibitor PAI-1 Suggest a Concerted Role in Regulating Physiological Angiogenesis, *Proceedings of the National Academy of Science USA*, vol. 89 (22), pp. 10686-10690, Nov. 15, 1992.
Baer et al., Corneal Laser Photocoagulation for Treatment of Neovascularization. Efficacy of 577 nm Yellow Dye Laser, *Ophthalmology*, vol. 99 (2), pp. 173-179, Feb. 1, 1992.
Baird et al., Receptor- and Heparin-Binding Domains of Basic Fibroblast Growth Factor, *Proceedings of the National Academy of Sciences*, vol. 85, pp. 2324-2328, Apr. 1988.
Balian et al., Structure of Rat Skin Collagen α1-CB8. Amino Acid Sequence of the Hydroxylamine-Produced Fragment HA2, *Biochemistry*, vol. 11 (20), pp. 2798-3806, 1972.
Banerjee et al., 2-Methoxyestradiol Blocks Estrogen-Induced Rat Pituitary Tumor Growth and Tumor Angiogenesis: Possible Role of Vascular Endothelial Growth Factor, *Anticancer Research*, vol. 20, pp. 2641-2646, Jan. 1, 2000.
Banik et al., Orally Active Long-Acting Estrogen (AY-20,121) (3-(2-propynyloxy)-estra-1,3,5,(10)-triene-17. beta.-ol trimethylacetate) (Identifier only), *Steroids*, vol. 16 (3), pp. 289-296, 1970.
Barchiesi et al., Differential Regulation of Estrogen Receptor Subtypes α and β in Human Aortic Smooth Muscle Cells by Oligonucleotides and Estradiol, *The Journal of Clinical Endocrinology & Metabolism*, vol. 89(5), pp. 2373-2381, Jun. 6, 2005.
Barczyk et al., Mast Cells in the Gastrointestinal Tract, *Roczniki Akademii Medvcznei W Bialvmstoku (Bialystok)*, vol. 40 (1), pp. 36-57, Jan. 1, 1995.
Bardon et al., Steroid Receptor-Mediated Cytotoxicity of an Antiestrogen and an Antiprogestin in Breast Cancer Cells, *Cancer Research*, vol. 47 (5), pp. 1441-1448, Mar. 1. 1987.
Barnes et al., Tumor Necrosis Factor Production in Patients with Leprosy, *Infection and Immunity*, vol. 60 (4), pp. 1441-1446, Apr. 1992.
Bhat et al., Estradiol-induced Mitotic Inhibition in the Bursa of Fabricius of Male Domestic Duckling (Chemical Abstracts Doc. No. 98:31837, 1982), *Mikroskopie*, vol. 39, pp. 113-117, May 1982.

Bhattacharyya et al., Tubulin aggregation and disaggregation: Mediation by two distinct vinblastine-binding sites, *National Academy of Sciences*, vol. 73 (7), pp. 2375-2378, Jul. 1976.

Bhooma et al., Eales' Disease: Accumulation of Reactive Oxygen Intermediates and Lipid Peroxides and Decrease of Antioxidants Causing Inflammation, Neovascularization and Retinal Damage, *Current Eye Research*, vol. 16 (2), pp. 91-95, Feb. 1, 1997.

Bindra et al., Studies in Antifertility Agents.8.Seco Steroids. 2. 5,6-Secoestradiol and Some Related Compounds, *Journal of Medicinal Chemistry*, vol. 18 (9), pp. 921-925, 1975.

Bissell et al., Putting Tumours in Context, *Nature Reviews Cancer*, vol. 1 (1), pp. 46-54, Oct. 1, 2001.

Blagosklonny et al., Raf-1/bcl-2 Phosphorylation: A Step from Microtubule Damage to Cell Death, *Cancer Research*, vol. 57, pp. 130-135, Jan. 1, 1997.

Blickenstaff et al., Estrogen-Catharanthus (Vinca) Alkaloid Conjugates (Chemical Abstracts Doc. No. 94:114277,1981), *Cytotoxic Estrogens in Hormone Receptive Tumors*, pp. 89-105, 1980.

Blickenstaff et al., Synthesis of Some Analogs of Estradiol, *Steroids*, vol. 46 (4,5), pp. 889-902, Oct. 1985.

Boehme et al., Juxtapapillary Choroidal Neovascular Membrane in a Patient with Paget's Disease and Lattice Corneal Dystrophy, *Journal of the American Optometric Association*, vol. 60 (8), pp. 612-616, Aug. 1, 1989.

Boyce et al., Some Preliminary Synthetical Studies with 5,6,7,8-Tetra-hydro-8-methylindane -1,5-dione, *Unknown*, pp. 4547-4553, 1960.

Boye et al., 185. Deaminocolchinyl Methyl Ether: Synthesis from 2,3,4,4'-Tetramethoxybiphenyl- 2-carbaldehyde. Comparison of Antitubulin Effects of Deaminocolchinyl Methyl Ether and Dehydro Analogs, *Helvetica Chimica Acta*, vol. 72, pp. 1690-1696, 1989.

Brandi et al., Bone endothelial cells as estrogen targets, *Calcif. Tissue Int.*, vol. 53 (5), pp. 312-317, 1993.

Brem, H. et al., Interstitial chemotherapy with drug polymer implants for the treatment of recurrent gliomas, *Journal of Neurosurgery*, vol. 74, pp. 441-446, Mar. 1, 1991.

Brodie, A.M., Aromatase Inhibitors in the Treatment of Breast Cancer, *Journal of Steroid Biochemistry and Molecular Biology*, vol. 49 (4-6), pp. 281-287, Jun. 1994.

Brosens et al., Comparative Study of the Estrogenic Effect of Ethinylestradiol and Mestranol on the Endometrium, *Contracteotion (Laboratory for Gynecological Physiopathology)*, vol. 14 (6), pp. 679-685, Dec. 1, 1976.

Brueggemeier et al., 2-Methoxymethylestradiol: A New 2-Methoxy Estrogen Analog that Exhibits Antiproliferative Activity and Alters Tubulin Dynamics, *Journal of Steroid Biochemistry & Molecular Biology*, vol. 78, pp. 145-156, 2001.

Bruno et al., New drugs for treatment of mulitple myeloma, *The Lancet*, vol. 5, pp. 430-442, Jul. 1, 2004.

Bu et al., Mechanisms for 2-methoxyestradiol-induced apoptosis of prostrate cancer cells, *FEBS Letters*, vol. 531, pp. 141-151, Jan. 2002.

Bu et al., p38 Mitogen-activated protein kinases is required for counteraction of 2-methoxyestradiol to estradio-stimulated cell proliferation and induction of apoptosis in ovarian carcinoma cells via phosphorylation Bcl-2, *Apoptosis*, vol. 11 (3), pp. 413-425, 2006.

Burrows, N. P., Thalidomide Modifies Disease, British Medical Journal, vol. 307 (6909), pp. 939-940, Oct. 9, 1993.

Cambie et al., Aromatic Steroids. Part II. Chromium Trioxide Oxidation of Some Oestra-1,3-5(10)-trienes, Journal of the Chemical Society, vol. 9, pp. 1234-1240, 1969.

Cambie et al., Aromatic Steroids. Part I. Oxidation Products of 3-Methoxyestra-1,3,5(10)-triene- 17β-yl Acetate, J. Chem. Soc., pp. 2603-2608, 1968.

Campochiaro et al., Retinal and Choroidal Neovascularization, Journal of Cellular Physiology, vol. 184, pp. 301-310, Jan. 1, 2000.

Cao et al., Update on Therapeutic Neovascularization, Cardiovascular Research, vol. 65, pp. 639-648, Jan. 1, 2005.

Carmeliet et al., Angiogenesis in Health and Disease, *Nature Medicine*, vol. 9 (6), pp. 653-660, Jun. 1, 2003.

Carothers et al., 2-Methoxyestradiol induces p53-associated apoptosis of colorectal cancer cells, *Cancer Letters*, vol. 187, pp. 77-86, Jan. 2002.

Castagnetta, L. et al., Simple Approach to Measure Metabolic Pathways of Steroids in Living Cells, *Journal of Chromatography*, vol. 25-39, pp. 25-39, Dec. 6, 1991.

Chamaon et al., Micromolar Concentrations of 2-Methoxyestradiol Kill Glioma Cells by an Apoptotic Mechanism, without Destroying their Microtubule Cytoskeleton, *Journal of Neuro-Oncology*, vol. 72, pp. 11-16, Jan. 2005.

Chang et al., Corneal Neovascularization, *Current Opinions in Ootholmology*, vol. 12, pp. 242-249, Jan. 1, 2001.

Chasserot-Golaz et al., Biotransformation of 17.beta.-hydroxy-11. beta.-(4-dimethylaminophenyl)17.alpha.1-propynyl-estra-4,9-diene-3-one of (RU486) in Rat Hepatoma Variants (Identifier only), *Biochemical Pharmacology*, vol. 46 (11), pp. 2100-2103, 1993.

Chauhan et al., 2-Methoxyestradiol and bortezomib/proteasome-inhibitor overcome dexamethasone-resistance in multiple myeloma cells by modulating Heat Shock Protein-27, *Apoptosis*, vol. 9, pp. 149-155, Jan. 1, 2004.

Chauhan et al., Mechanisms of cell death and survival in multiple myeloma (MM):Therapeutic implications, *Apoptosis*, vol. 8 (4), pp. 337-343, Jan. 2003.

Chauhan et al., Superoxide-dependent and -independent mitochondrial signaling during apoptosis in multiple myeloma cells, *Oncogene*, vol. 22, pp. 6296-6300, Jan. 2003.

Chauhan et al., 2-Methoxyestradiol overcomes drug resistance in multiple myeloma cells, *Blood*, vol. 100 (6), pp. 2187-2194, Sep. 15, 2002.

Chen et al., A New Synthetic Route to 2- and 4-Methoxyestradiols by Nucleophilic Substitution, *Steroids*, vol. 47 (1), pp. 63-66, Jan. 1986.

Chen et al., Synthesis of 11.beta.-(4-dimethylaminophenyl)-17.beta-hydroxy-17.alpha.-(1-propynyl) estra-4, 9-dien-3-one (RU486) (Identifier only), *Naniing Yaoxuevuan Xuebao*, vol. 17 (4), pp. 282-285, 1986.

Chng et al., *Targeted Therapy in Multiple Myeloma, Cancer Control*, vol. 12 (2), pp. 91-104, Apr. 2005.

Cleveland et al., A Radical Approach to Treatment, *Nature*, vol. 407, pp. 309-311, Sep. 21, 2000.

Cohen et al., Novel Total Synthesis of (+)-Estrone 3-Methyl Ether, (+)-13β-Ethyl-3-methoxygona-1,3,5(10)-trien-17-one, and (+)-Equilenin 3-Methyl Ether, *The Journal of Oreanic Chemistry*, vol. 40 (6), pp. 681-685, Mar. 21, 1975.

Collins et al., The Structure and Function of Estrogens. XI. Synthesis of (+/−)-7(8-11α)*abeo*-Estradiol and its 9,11-Didehydro Derivative, *Aust. Journal of Chemistry*, vol. 45 (1), pp. 71-97, 1992.

Corey et al., Applications of N,N-Dimethylhydrazones to Synthesis. Use in Efficient, Positionally and Stereochemically Selective C-C Bond Formation; Oxidative Hydrolysis to Carbonyl Compounds, *Tetrahedron Letters*, vol. 1, pp. 3-6, 1976.

Corey et al., Facile Conversion of N,N-Dimethylhydrazones to Cabonyl Compounds by Cupric Ion-Catalyzed Hydrolysis, *Tetrahedron Letters*, vol. 41, pp. 3667-3668, 1976.

Crabbe, P., Cotton Effect of the Styrene Chromophore. *Chem. Ind.*, vol. 27, pp. 917-918, 1969.

Crum, R. et al., A New Class of Steroids Inhibits Angiogenesis in the Presence of Heparin or a Heparin Fragment, *Science*, vol. 230, pp. 1375-1378, Dec. 20, 1985.

Cummings et al., Apoptosis, *The American Journal of Surgical Pathology*, vol. 21 (1), pp. 88-101, 1997.

Cursiefen et al., Angiogenesis in Corneal Disease: Histopathologic Evaluation of 254 Human Corneal Buttons with Neovascularization, *Cornea*, vol. 17 (6), pp. 611-613, Nov. 1, 1998.

Cushman et al., Synthesis, Antitubulin and Antimitotic Activity, and Cytotoxicity of Analogs of 2-Methoxyestradiol, an Endogenous Mammalian Metabolite of Estradiol that Inhibits Tubulin Polymerization by Binding to the Colchicine Binding Site, *Journal of Medicinal Chemistry*, vol. 38 (12), pp. 2041-2049, pp. Jun. 9, 1995.

Cushman et al., Synthesis of Analogs of 2-Methoxyestradiol with Enhanced Inhibitory Effects on Tublin Polymerization and Cancer Cell Growth, *Journal of Medicinal Chemistry*, vol. 40 (15), pp. 2323-2334, 1997.

D'Amato et al., 2-Methoxyestradiol, and Endogenous Mammalian Metabolite, Inhibits Tublin Polymerization by Interacting at the Colchicine Site, *Proceedings of the National Academy of Science USA*, vol. 91, pp. 3964-3968, Apr. 26, 1994.

D'Amato, R.J. et al., Thalidomide is an Inhibitor of Angiogenesis, *Proceedings of the National Academy of Science USA*, vol. 91, pp. 4082-4085, Apr. 1, 1994.

D'Amore et al., Mechanisms of Angiogenesis, *Annual Review of Physiology*, vol. 49, pp. 453-464, Jan. 1, 1987.

Dahut et al., Phase I Clinical Trail of Oral 2-Methoxyestradiol, an Antiangiogenic and Apoptotic Agent, in Patients with Solid Tumors, *Cancer Biology & Therapy*, vol. 5 (1), pp. e1-e6, Jan. 2006.

Danis et al., Anti-Angiogenic Therapy of Proliferative Diabetic Retinopathy, *Expert Opinion in Pharmacotherapy*, vol. 2 (3), pp. 395-407, Mar. 1, 2001.

Davoodpour et al., Effects of 2-methoxyestradio on proliferation, apoptosis and PET-tracer uptake in human prostate cancer cell aggregates, *Nuclear Medicine and Biology*, vol. 31, pp. 867-874, Jan. 1, 2004.

Davoodpour et al., 2-Methoxyestradiol-induced Apoptosis in Prostate Cancer Cells Requires Smad7, *The Journal of Biological Chemistry*, vol. 280 (15), pp. 14773-14779, Apr. 15, 2005.

Dawling et al., In Vitro Model of Mammary Estrogen Metabolism: Structural and Kinetic Differences between Catechol Estrogens 2- and 4-Hydroxyestradiol, *Chem. Res. Toxicol.*, vol. 17, pp. 1258-1264, Jan. 1, 2004.

Dawling et al., Methoxyestrogens Exert Feedback Inhibition on Cytochrome P450 and 1A1 and 1B1, *Cancer Research*, vol. 63, pp. 3127-3132, Jun. 15, 2003.

Day et al., The effects of 2-substituted oestrogen sulphamates on the growth of prostate and ovarian cancer cells, *Journal of Steroid Biochemistry & Molecular Biology*, vol. 84, pp. 317-325, Jan. 2003.

De Bono et al., The Future of Cytotoxic Therapy: Selective Cytotoxicity Based on Biology is the Key, *Breast Cancer Research*, vol. 5 (3), pp. 154-159, Mar. 27, 2003.

De Laey et al., Hyperlipofuscinosis and Subretinal Fibrosis in Stargardt's Disease, *Retina*, vol. 15 (5), pp. 399-406, Jan. 1, 1995.

Ding et al., Sex Hormone-Binding Globulin Mediates Prostate Androgen Receptor Action via a Novel Signaling Pathway, *Endocrinology*, vol. 139 (1), pp. 213-218, 1998.

Dingli et al., Promising Preclinical Activity of 2-Methoxyestradiol in Multiple Myeloma, *Clinical Cancer Research*, vol. 8, pp. 3948-3954, Dec. 1, 2002.

Djavaheri-Mergny et al., TNFα Potentiates 2-Methoxyestradiol-Induced Mitochondrial Death Pathway, *Annals New York Academy of Sciences*, vol. 1010, pp. 159-162, Jan. 2003.

Dobos et al., In Vitro and In Vivo Antitumor Effect of 2-Methoxyestradiol on Human Melanoma, *International Journal of Cancer*, vol. 112, pp. 771-776, Jan. 2004.

Dubey et al., Methoxyestradiols Mediate the Antimitogenic Effects of Estradiol on Vascular Smooth Muscle Cells via Estrogen Receptor-Independent Mechanisms, *Biochemical and Biophysical Research Communications*, vol. 278, pp. 27-33, 2000.

Dubey et al., Cardiovascular Pharmacology of Estradiol Metabolites, *The Journal of Pharmacology and Experimental Therapeutics*, vol. 308 (2), pp. 403-409, Jan. 2004.

Dubey et al., Catecholamines Block the Antimitogenic Effect of Estradiol on Human Glomerular Mesangial Cells, *Hypertension*, vol. 42, pp. 349-355, Jan. 2003.

Dubey et al., Mexthoxyestradiols Mediate the Antimitogenic Effects of Locally Applied Estradiol on Cardiac Fibroblast Growth, *Hypertension*, vol. 39 (Part 2), pp. 412-417, Feb. 2002.

Dubey et al., Role of Methoxyestradiols in the Growth Inhibitory Effects of Estradiol on Human Glomerular Mesangial Cells, *Hypertension*, vol. 39 (Part 2), pp. 418-424, Feb. 2002.

Dubey et al., Estradiol Metabolites Inhibit Endothelin Synthesis by an Estrogen Receptor-Independent Mechanism, *Hypertension*, vol. 37 Part 2, pp. 640-644, Feb. 1, 2001.

Durani et al., Seco-Oestradiols and Some Non-Steroidal Oestsrogens: Structural Correlates of Oestrogenic Action, *Journal of Steroid Biochemistry*, vol. 11, pp. 67-77, 1979.

Dvir et al., Thin-layer Chromatography of DANSYL-oestrogens, *Journal of Chromatography*, vol. 52, pp. 505-506, Nov. 4, 1970.

Eder et al., Synthese von Ostradiol (in German—No Translation available), *Chem. Ber.*, vol. 109, pp. 2948-2953, 1976.

Edsall et al., Effects of Altering the Electronics of 2-Methoxyestradiol on Cell Proliferation, on Cytotoxicity in Human Cancer Cell Cultures, and on Tubulin Polymerization, *Journal of Medicinal Chemistry*, vol. 47, pp. 5126-5139, Jan. 2004.

El-Tombary ., Synthesis, Uterotropic, And Antiuterotrophic Activities of Some Estradiol Derivatives Containing Thiadiazole, Thiazoline, aNd Thiazolidinone Moieties, *Arch. Pharm. Pharm. Med. Chem.*, vol. 330 (9-10), pp. 295-302, 1997.

Emons et al., Modulation der hypophysaren Sekretion von Luteinisierendem Hormon (LH) durch Ostrogene, *Focus MHL*, vol. 3, pp. 221-228, 1986.

Enjyoji, K. et al., Effect of Heparin on the Inhibition of Factor Xa by Tissue Factor Pathway Inhibitor: A Segment, Gly$^{212}$- Phe$^{243}$, of the third Kunitz Domain is a Heparin-Binding Site, *Biochemistry*, vol. 34 (17), pp. 5725-5735, Jan. 1, 1995.

Epe et al., Microtubular Proteins as Cellular Targets for Carcinogenic Estrogens and Other Carcinogens, *Mechanisms of Chromosome Distribution and Aneuploidy*, pp. 345-351, 1989.

Escuin et al., Both Microtubule-Stabilizing and Microtubule-Destabilizing Drugs Inhibit Hypoxia-Inducible Factor-1α Accumulation and Activity by Disrupting Microtubule Function, *Cancer Research*, vol. 65 (19), pp. 9021-9028, Oct. 1, 2005.

Evans et al., A Convergent Total Synthesis of +/− Colchicine and +/− Desacetamidoisocolchicine, *Journal of the American Chemical Society*, vol. 103, pp. 5813-5821, Sep. 23, 1981.

Fajardo et al., Effects of Genistein and 2-Methoxyestradiol on Matrix Matalloproteinases and their Inhibitors Secreted by Ehrlich Ascites Tumor Cells, *Anticancer Research*, vol. 20, pp. 1691-1694, Jan. 1, 2000.

Fanchenko et al., Characterisitics of the guinea pig uterus estrogen receptor system, *Byull. Eksp. Biol. Med.*, vol. 85 (4), pp. 467-470, 1978.

Farmer et al., Retinal Vasculitis Associated with Autoantibodies to Sjogren's Syndrome A Antigen, *American Journal of Ophthalmology*, vol. 100 (6), pp. 814-821, Dec. 1, 1985.

Feher et al., Multiple Flexible Alignment with SEAL: A Study of Molecules Acting on the Colchicine Binding Site, *Journal of Chemical Information and Computer Sciences*, vol. 40, pp. 495-502, Jan. 1, 2000.

Fetizon et al., Synthesis of 2-keto steroids, *Bull. Soc. Chim. FR.*, vol. 8, pp. 3301-3306, 1968.

Fevig et al., A Short, Stereoselective Route to 16α-(Substituted-alkyl)estradiol Derivatives, *Journal of Organic Chemistry*, vol. 52, pp. 247-251, 1987.

Field et al., Effect of Thalidomide on the Graft versus Host Reaction, *Nature*, vol. 211(5055), pp. 1308-1310, Sep. 17, 1966.

Fieser et al., N-Methylformanilide, *Organic Synthesis Collective* vol. 3, pp. 590-591, 1955.

Figg et al., Inhibition of angiogenesis: treatment options for patients with metastatic prostate cancer, *Investigational New Drugs*, vol. 20, pp. 183-194, Jan. 2002.

Fishman, J., Synthesis of 2-Methoxyestrogens, *Journal of the American Chemical Society*, vol. 80, pp. 1213-1216, Mar. 5, 1958.

Fitzgerald, Molecular Features Colchicine Associated with Antimitotic Activity and Inhibition of Tubulin Polymerization *Biochemical Pharmacology*, vol. 25 (12), pp. 1383-1387, Jun. 15, 1976.

Flohe et al., Studies on the Hypothetical Relationship of Thalidomide-induced Embryopathy and Collagen Biosynthesis, *Arzneimitte/Forschung (Germany West)*, vol. 31 (2), pp. 315-320, Jan. 1, 1981.

Folkman et al., Angiogenesis Inhibition and Tumor Regression Caused by Heparin or a Heparin Fragment in the Presence of Cortisone, *Science*, vol. 221, pp. 719-725, Aug. 19, 1983.

Folkman, J., Tumor Angiogenesis: Therapeutic Implications, *New England Journal of Medicine*, vol. 285 (21), pp. 1182-1186, Nov. 18, 1971.

Folkman, J. et al., Induction of Angiogenesis During the Transition from Hyperplasia to Neoplasia, *Nature*, vol. 339, pp. 58-61, May 4, 1989.

Folkman, J. et al., Tumor Behavior in Isolated Perfused Organs in vitro Growth and Metastases of Biopsy Material in Rabbit Thyroid and Canine Intestinal Segment, *Annals of Surgery*, vol. 164(3), pp. 491-502, Sep. 1, 1966.

Fotsis et al., The Endogenous Oestrogen Metabolite 2-Methoxyoestradiol Inhibits Angiogenesis and Suppresses Tumour Growth, *Nature*, vol. 368, pp. 237-239, Mar. 17, 1994.

Fraser et al., Angiogenesis and Its Control in the Female Reproductive System, *British Medical Bulletin*, vol. 56 (3), pp. 787-797, 2000.

Friedlander et al., Involvement of Integrins αvβ33 and αvβ5 in Ocular Neovascular Diseases, *Proceedings of the National Academy of Science (USA)*, vol. 93, pp. 9764-9769, Sep. 1, 1996.

Furukawa et al., Effect of Indole-3-Acetic Acid Derivatives on Neuroepithelium in Rat Embryos, *The Journal of Toxicological Sciences*, vol. 30 (3), pp. 165-174, Jan. 2005.

Gadosy et al., Generation, Characterization, and Deprotonation of Phenol Radical Cations, *Journal of Physical Chemistry*, vol. 103, pp. 8834-8839, 1999.

Gandhi et al., Mannich Reaction of Estrone, *Journal of Indian Chem. Soc.*, vol. 39, pp. 306-308, 1962.

Gao et al., 2-Methoxyestradiol-induced apoptosis in human leukemia cells proceeds through a reactive oxygen species and Akt-dependent process, *Oncogene*, pp. 1-13, Jan. 2005.

Gaslini et al., Reaction of Eugenol with Synthesis Gas. Synthesis of 5,6,7,8-Tetrahydro -3-methoxy -2-napthol, *Journal of Organic Chemistry*, vol. 29 (5), pp. 1177-1180, May 1964.

Genentech USA, VEGF may be main cause of diabetic retinopathy, *Biotechnology Newswatch*, pp. 13-14, Oct. 17, 1994.

Getahun et al., Synthesis of Alkoxy-Substituted Diaryl Compounds and Correlation of Ring Separation with Inhibition of Tubulin Polymerization: Differential Enhancement of Inhibitory Effects Under Suboptimal Polymerization Reaction Conditions, *Journal of MedicinalChemistry*, vol. 35 (6), pp. 1058-1067, Mar. 20, 1992.

Gian Tondury et al., Zur Wirkung Der Sexualhormone Auf Wachstum and Differenzierung (See English Summary p. 55), *Cambridge Philosophical Society*, pp. 28-58, Dec. 17, 1955.

Gimbrone, M.A. et al., Tumor Growth and Neovascularization: An Experimental Model Using the Rabbit Cornea, *Journal of the National Cancer Institute*, vol. 52(2), pp. 413-419, Feb. 1, 1974.

Gimbrone, M.A. et al., Tumor dormancy in vivo by Prevention of Neovascularization, *Journal of Experimental Medicine*, vol. 136, pp. 261-276, Jan. 1, 1972.

Gleichmann et al., Immunoblastic Lymphadenopathy, Systemic Lupus Erythematosus, and Related Disorders. Possible Pathogenetic Pathways, *American Journal of Pathology*, vol. 72 (4), pp. 708-723, Oct. 1, 1979.

Gokmen-Polar et al., β-Tubulin Mutations are Associated with Resistance to 2-Methoxyestradiol in MDA-MB-435 Cancer Cells, *Cancer Research*, vol. 65 (20), pp. 9406-9414, Oct. 15, 2005.

Gonalez et al., Synthesis and Pharmacological Evaluation of 8α-Estradiol Derivatives, *Steroids*, vol. 40 (2), pp. 171-187, Aug. 1, 1982.

Gross et al., Inhibition of Tumor Growth, Vascularizaton, and Collagenolysis in the Rabbit Cornea by Medroxyprogesterone, *Proceedings of the National Academy of Science USA*, vol. 78 (2), pp. 1176-1180, Feb. 1981.

Gross, J.L. et al., Modulation of Solid Tumor Growth in vivo by bFGF, *Proceedings of the American Association of Cancer Research*, vol. 31, pp. 79, Mar. 1, 1990.

Gui et al., 2-Methoxyestradiol Induces Cell Cycle Arrest and Mitotic Cell Apoptosis in Human Vascular Smooth Muscle Cells, *Hypertension*, vol. 47, pp. 271-280, Dec. 27, 2005.

Gujjar et al., The Effect of Estradiol on Candida albicans Growth, *Annals of Clinical and Laboratory Science*, vol. 27 (2), pp. 151-156, 1997.

Gunzler, V., Thalidomide-A Therapy for the Immunological Consequences of HIV Infection?, *Medical Hypothesis*, vol. 30 (2), pp. 105-109, Oct. 1989.

Gupta et al., Antifertility Agents. XIV. Secosteroids. VII. Synthesis of 2α- and 2β, 6β- dimethyl- 3β-(p-hyroxyphenyl)-trans-bicyclo[4.3.0]nonan-7-ones and some related compounds, *Indian Journal of Chemistry*, vol. 13 (7), pp. 759-760, 1975.

Gupta et al., Studies in Antiferility Agents. Part XVIII. 2α, 6β-Diethyl-3β-(p-hydroxyphenyl)-trans-bicyclo[4.3.0]nonan-7β-ol and 6β-methyl-3β-(p-hydroxyphenyl)-2α-propyl- trans-bicyclo[4.3.0]nonan-7β-ol, *Indian Journal of Chemistry*, vol. 19B (10), pp. 886-890, 1980.

Gutierrez-Rodriguez et al., Treatment of Refractory Rheumatoid Arthritis—The Thalidomide Experience, *The Journal of Rheumatology*, vol. 16 (2), pp. 158-163, Feb. 1989.

Gutierrez-Rodriguez, O., Thalidomide—A Promising New Treatment for Rheumatoid Arthritis, *Arthritis and Rheumatism*, vol. 27 (10), pp. 1118-1121, Oct. 1984.

Hagen et al., Inhibition of mitochondrial respiration by the anticancer agent 2-methoxyestradiol, *Biochemical and Biophysical Research Communications*, vol. 322, pp. 923-929, Jan. 2004.

Hahnel et al., The Specificity of the Estrogen Receptor of Human Uterus, *Journal of Steroid Biochemistry*, vol. 4, pp. 21-31, 1973.

Hajjar et al., New Concepts in Fibrinolysis and Angiogenesis, *Current Atherosclerosis Reports*, vol. 2 (5), pp. 417-421, Sep. 1, 2000.

Haldar et al., Bc12 is the Guardian of Microtubule Integrity, *Cancer Research*, vol. 57, pp. 229-233, Jan. 15, 1997.

Hamanaka et al., Retinal Ischemia and Angle Neovascularization in Proliferative Diabetic Retinopathy, *American Journal of Ophthalmology*, vol. 132 (5), pp. 648-658, Nov. 1, 2001.

Hamel et al., Interactions of 2-Methoxyestradiol, an Endogenous Mammalian Metabolite, with Unpolymerized Tubulin and with Tubulin Polymers, *Biochemistry*, vol. 35 (4), pp. 1304-1310, 1996.

Hammers et al., Introduction a novel proliferation assay for pharmacological studies allowing the combination of BrdU detection and phenotyping, *Journal of Immunological Methods*, vol. 264, pp. 89-93, Jan. 2002.

Hammond et al., Structure/function analyses of human sex hormone-binding globulin: effects of zinc on steroid-binding specificity, *Steroid Biochemistry & Molecular Biology*, vol. 85, pp. 195-200, Jan. 2003.

Han et al., Dehydroepiandrosterone and Dihydrotestosterone Recognition by Human Estrogenic 17β-Hydroxysteroid Dehydrogenase, *Journal of Biological Chemistry*, vol. 275 Iss 2, pp. 1105-1111, Jan. 14, 2000.

Han et al., Synergism between the Anticancer Actions of 2-Methoxyestradiol and Microtubule-Disrupting Agents in Human Breast Cancer, *Cancer Research*, vol. 65 (2), vol. 65 (2), pp. 387-393, Jan. 15, 2005.

Handley et al., Chronic bullous disease of childhood and ulcerative colitis, *British Journal of Dermatology*, vol. 127 (40), pp. 67-68, Jul. 1, 1992.

Hartley-Asp et al., Diethylstilbestrol Induces Metaphase Arrest and Inhibits Microtubule Assembly, *Mutation Research*, vol. 143 (4), pp. 231-235, Aug. 1985.

He et al., A Versatile Synthesis of 2-Methoxyestradiol, an Endogenous Metabolite of Estradiol which Inhibits Tubulin Polymerization by Binding to the Colchicine Binding Site, *Bioogranic & Medicinal Chemistry Letters*, vol. 4 (14), pp. 1724-1728, 1994.

He et al., Novel Cytokine Release Inhibitors. Part II: Steroids, *Bioorganic & Medicinal Chemistry Letters*, vol. 8, pp. 2825-2828, 1998.

Hejaz et al., Synthesis and Biological Activity of the Superestrogen (E)-17-Oximino-3O-sulfamoyl-1,3,5,(10)-estratriene: X-ray Crystal Structure of (E)-17-Oximino-3-hydroxy-1,3,5(10)-estratriene, *Journal of Medicinal Chemistry*, vol. 42 (16), pp. 3188-3192, 1999.

Heney et al., Thalidomide treatment for chronic graft-versus-host disease, *British Journal of Haematology*, vol. 78 (1), pp. 23-27, May 1991.

Hill et al., Pathogenesis of Pterygium, *Eye*, vol. 3, (Pt 2), pp. 218-226, Jan. 1, 1990.

Himes et al., Action of the Vinca Alkaloids Vincristine, Vinblastine, and Desacetyl Vinblastine Amide on Microtubules in Vitro, *Cancer Research*, vol. 36, pp. 3798-3802, Oct. 1976.

Ho, Shuk-Mei, Estrogens and Anti-Estrogens: Key Mediators of Prostate Carcinogenesis and New Therapeutic Candidates, *Journal of Cellular Biochemistry*, vol. 91, pp. 491-503, Jan. 1, 2004.

Holden et al., Mitotic Arrest by Benzimidazole Analogs in Human Lymphocyte Cultures, *Environmental Mutagenesis*, vol. 2, pp. 67-73, 1980.

Holker et al., The Reactions of Estrogens with Benzeneseleninic Anhydride and Hexamethyldisilazane, *J. Chem. Soc. Perkin Trans.*, vol. 1, pp. 1915-1918, 1982.

Hori, A. et al., Suppression of Solid Tumor Growth by Immunoneutralizing Monoclonal Antibody Against Human Basic Fibroblasts Growth Factor, *Cancer Research*, vol. 51, pp. 6180-6184, Nov. 15, 1991.

Hou et al., 2-Methoxyestradiol at low dose induces differentiation of myeloma cells, *Leukemia Research*, vol. 29, pp. 1059-1067, Jan. 2005.

Hu et al., Interleukin-8 Stimulates Angiogenesis in Rats, *Inflammation*, vol. 17 (2), pp. 135-143, Apr. 1, 1993.

Hu, G., Neomycin Inhibits Angiogenin-induced Angiogenesis, *Proceedings of the National Academy of Sciences, USA*, vol. 95 (17), pp. 9791-9795, 1998.

Huang et al., Superoxide Dismutase as a Target for the Selective Killing of Cancer Cells, *Nature*, vol. 407 (6802), pp. 390-395, Sep. 21, 2000.

Huber et al., Tubulin Binding of Conformationally Restricted Bis-Aryl Compounds, *Bioorganic & Medicinal Chemistry Letters*, vol. 1 (5), pp. 243-246, 1991.

Hughes et al., 2-Methoxyestradiol and Analogs as Novel Antiproliferative Agents: Analysis of Three Dimensional Quantitative Structure-Activity Relationships for DNA Synthesis Inhibition and Estrogen Receptor Binding, *Molecular Pharmacology*, vol. 61 (5), pp. 1053-1069, Jan. 1, 2002.

Huober et al., Oral Administration of an Estrogen Metabolite-Induced Potentiation of Radiation Antitumor Effects in Presence of Wild-Type p53 in Non-Small-Cell Lung Cancer, *International Journal of Radiation Oncology, Biology, Physics*, vol. 48 (4), pp. 1127-1137, Jan. 1, 2000.

Ikegawa et al., Immunoaffinity Extraction for Liquid Chromatographic Determination of Equilin and Its Metabolites in Plasma, *Biomed. Chromatogr*, vol. 10 (2), pp. 73-77, 1996.

Imamura et al., Method for Manufacture of Dihydric Phenols, *USPATFULL* 76:20259 US 3,950,437, Apr. 13, 1976.

Inger, D. et al., Synthetic analogues of fumagillin that inhibit angiogenesis and suppress tumor growth, *Nature*, vol. 348, pp. 555-557, Dec. 6, 1990.

Inoue et al., Molecular Mechanism of Diclofenac-Induced Apoptosis of Promyelocytic Leukemia: Dependency on Reactive Oxygen Species, AKT, BID, Cytochrome c, and Caspase Pathway, *Free Radical Biology & Medicine*, vol. 37 (8), pp. 1290-1299, Jan. 1, 2004.

Ireson et al., Pharmacokinetics and efficacy of 2-methoxyestradiol and 2-methoxyestradiol- bis-sulphamate in vivo in rodents, *British Journal of Cancer*, vol. 90, pp. 932-937, Jan. 1, 2004.

Iriarte et al., Steroids (XCIV). Synthesis of 2-methyl and 1,2-dimethyl estrogens, *Tetrahedron*, vol. 3, pp. 28-36, 1958.

Jackson et al., The Codependence of Angiogenesis and Chronic Inflammation, *The FASEB Journal*, vol. 11, pp. 457-465, Jan. 1, 1997.

Jaggers et al., Potent Inhibitory Effects of Steroids in an in vitro Model of Angiogenesis, *Journal of Endocrinology*, vol. 150 (3), pp. 457-464, 1996.

Jampol et al., Peripheral Proliferation Retinopathies: An Update on Angiogenesis, Etiologies and Management, *Survey of Ophthalmology*, vol. 38 (6), pp. 519-540, May 1, 1994.

Jeung et al., Thymidine phosphorylase suppresses apoptosis induced by microtubule-interfering agents, *Biochemical Pharmacology*, vol. 70, pp. 13-21, Jan. 2005.

Jhingran et al., Studies in Antifertility Agents—Part XLI: Secosteroids-x: Syntheses of Various Stereoisomers of (+−)-2,6β-diethyl-7α-ethynyl-3-(p-hydroxphenyl)-trans-bicyclo [4.3.0]nonan-7β-ol., *Steroids*, vol. 42 (6), pp. 627-634, 1983.

Josefsson et al., Suppression of Type II Collagen-Induced Arthritis by the Endogenous Estrogen Metabolite 2-Methoxyestradiol, *Arthritis & Rheumatism*, vol. 40 (1), pp. 154-163, Jan. 1997.

Joubert et al., Influence of prostaglandin $A_2$ and 2-methoxyestradiol on Bax and Bcl-2 experssion levels in cervical carcinoma cells, *Biomedical Research*, vol. 26 (2), pp. 87-90, Jan. 2005.

Jourbert et al., Bax/Bcl-2 expression levels of 2-methoxyestradiol-exposed esophageal cancer cells, *Biomedical Research*, vol. 105026 (3), pp. 131-134, Jan. 2005.

Jozsef, Timar, Beszamolo a Nemzeti Onkologiai Kutatas-fejlesztesi Konzorcium 2003. evi tevekenysegerol *Magyaa Onkoloeusok Tarsasaga*, vol. 48, pp. 75-79, Jan. 2004.

Kabarity et al., Further Investigations on the cytological effects of some contraceptives, *Mutation Research*, vol. 135, pp. 181-188, 1984.

Kachadourian et al., 2-Methoxyestradiol Does Not Inhibit Superoxide Dismutase, *Archives of Biochemistry and Biophysics*, vol. 392 (2), pp. 349-353, Aug. 15, 2001.

Kahlon et al., Angiogenesis in Atherosclerosis, *Canadian Journal of Cardiology*, vol. 8 (1), pp. 60-64, Jan. 1, 1992.

Kalina et al., Neovascularization of the Disc in Pars Planitis, *Retina*, vol. 10 (4), pp. 269-273, Jan. 1, 1990.

Karbowski et al., Opposite Effects of Microtubule-Stabilizing and Microtubule-Destabilizing Drugs on Biogenesis of Mitochondria in Mammalian Cells, *Journal of Cell Science*, vol. 114 (2), pp. 281-291, Oct. 27, 2000.

Karwat, Separation and Recovery of Hydrogen Sulfide from Hydrocarbon Mixture, *Caplus DE 1103310*, Sep. 2, 1959.

Kataoka et al., An Agent that Increases Tumor Suppressor Transgene Product Coupled with Systemic Transgene Delivery Inhibits Growth of Metastatic Lung Cancer in Vivo, *Cancer Research*, vol. 58 (21), pp. 4761-4765, Nov. 1998.

Kelly et al., The Stimulation of Prostaglandin Production by Two Antiprogesterone Steroids in Human Endometrial Cells, *Journal of Clinical Endocrinology Metabolism*, vol. 62 (6), pp. 1116-1123, Jun. 1986.

Kim et al., Mass spectrometric measurement of differential reactivity of cysteine to localize protein-ligand binding sites. Application to tubulin-binding drugs, *Analytical Biochemistry*, vol. 332, pp. 376-383, Jan. 1, 2004.

Kim, K.J. et al., Inhibition of Vascular Endothelial Growth Factor-induced Angiogenesis Suppresses Tumor Growth In Vivo, *Nature*, vol. 362, pp. 841-844, Apr. 29, 1993.

Kinuya et al., Improved survival mice bearing liver metastases of colon cancer cells treated wiht a combination radioimmunotherapy and antiangiogenic therapy, *European Journal of Nuclear Medicine and Molecular Imaging*, pp. 1-11, Jan. 1, 2004.

Kinuya et al., Anti-angiogenic therapy and chemotherapy affect $^{99m}Tc$ sestamibi and $^{99m}TcHL91$ accumulation differently in tumour xenograft, *Nuclear Medicine Communications*, vol. 26 (12), pp. 1067-1073, Jan. 2006.

Kiuru et al., Short synthesis of 2-methoxyestradiol and 2-hydroxyestradiol, *Steroids*, vol. 68, pp. 373-375, Jan. 2003.

Klauber at al., Inhibition of Angiogenesis and Breast Cancer in Mice by the Microtubule Inhibitors 2-Methoxyestradiol and Taxol, *Cancer Research*, vol. 57, pp. 81-86, Jan. 1, 1997.

Knighton, D. et al., Avascular and Vascular Phases of Tumour Growth in the Chick Embyo, *British Joumal of Cancer*, vol. 35, pp. 347-356, Jan. 1, 1977.

Kole et al., Studies in Antifertility Agents. 11. Secosteroids.5.Synthesis of 9,11-Secoestradiol, *Journal of Medicinal Chemistry*, vol. 18 (7), pp. 765-766, 1975.

Kornmehl et al., Bilateral Keratitis in Lyme Diseases, *Ophthalmology*, vol. 96 (8), pp. 1194-1197, Aug. 1, 1989.

Kousteni et al., Reversal of Bone Loss in Mice by Nongenotypic Signaling of Sex Steroids, *Science*, vol. 298, pp. 843-846, Oct. 25, 2002.

Kovacs et al., Steroids. XXIII. Synthesis of 2- and 4-hydroxy and 2,4-dihydroxy derivatives of estrone and estradiol, *Acta Phys. Chem.*, vol. 19 (3), pp. 287-290, 1973.

Kumar et al., 2-Methoxyestradiol Blocks Cell-Cycle Progression at $G_2/M$ Phase and Inhibits Growth of Human Prostate Cancer Cells, *Molecular Carcinogenesis*, vol. 31, pp. 111-124, Jan. 1, 2001.

Kurebayashi et al., Paradoxical Hormone Responses KPL-1 Breast Cancer Cells in vivo: a Significant Role of Angiogenesis in Tumor Growth, *Oncology*, vol. 59 (2), pp. 158-165, 2000.

Lakhani et al., Determination of the antiangiogenesis agent 2-methoxyestradiol in human plasma by liquid chromatography wiht ultraviolet radiation, *Journal of Chromatography B*, vol. 806, pp. 289-293, Jan. 1, 2004.

Lakhani et al., Determination of 2-methoxyestradiol in human plasma, using liquid chromatography/tandem mass spectrometry, *Rapid Commun. Mass Spectrom.*, vol. 19, pp. 1176-1182, Feb. 2005.

Lambert et al., 2-Methoxyestradiol Induces Caspase-Independent Mitochondria-Centered Apoptosis in DS-Sarcoma Cells, *International Journal of Cancer*, vol. 108, pp. 493-501, Jan. 2004.

Lavallee et al., 2-Methoxyestradiol Up-Regulates Death Receptor 5 and Induces Apoptosis through Activation of the Extrinsic Pathway, *Cancer Research*, vol. 63, pp. 468-475, Jan. 15, 2003.

Lavallee et al., 2-Methoxyestradiol Inhibits Proliferation and Induces Apoptosis Independently of Estrogen Receptors α and β, *Cancer Research*, vol. 62, pp. 3691-3697, Jul. 1, 2002.

Lavigne et al., The Effects of Catechol-*O*-Methyltransferase Inhibition on Estrogen Metabolite and Oxidative DNA Damage Levels in Estradiol-Treated MCF-7 Cells, *Cancer Research*, vol. 61, pp. 7488-7494, Oct. 15, 2001.

Le Bras, J. et al., Activation and Regioselective Ortho-Functionalization of the A-Ring of B-Estradiol Promoted by "CpIr": An Efficient Organometallic Procedure for the Synthesis of 2-Methoxyestradiol, *Organometallics*, vol. 16, pp. 1765-1771, 1997.

Lee et al., Inhibition of Growth and Angiogenesis of Human Neurofibrosarcoma by Heparin and Hydrocortisone, *Journal of Neurosurgery*, vol. 73 (3), pp. 429-435, Sep. 1, 1990.

Lee et al., Ocular Neovascularization: An Epidemiologic Review, *Survey of Ophthalmology*, vol. 43 (3), pp. 245-269, Nov. 1, 1998.

Leese et al., Anti-cancer activities of novel D-ring modified 2-substituted estrogen-3*O*-sulfamates, *Juornal of Steroid Biochemistry and Molecular Biology*, vol. 94, pp. 239-251, Jan. 2005.

Leveille et al., Platelet-Induced Retinal Neovascularization in Leukemia, *American Journal of Ophthalmology*, vol. 91 (5), pp. 640-644, May 1, 1981.

Lewis et al., Differential effects of 16α-hydroxyestrone and 2-methoxyestradiol on cyclin D1 involving the transcription factor ATF-2 in MCF7 breast cancer cells, *Journal of Molecular Endocrinology*, vol. 34, pp. 91-105, Jan. 2005.

Lewis, Richard J., *Hawley's Condensed Chemical Dictionary*, pp. 577, Jan. 1993.

Lewis, Richard J., *Hawley's Condensed Chemical Dictionary*, pp. 128-129, Jan. 1993.

Li et al., Antiproliferative activity and toxicity of 2-methoxyestradiol in cervical cancer xenograft mice, *Int. J. Gynecol. Cancer*, vol. 15, pp. 301-307, Jan. 2005.

Li et al., Antitumor Activities of 2-Methoxyestradiol on Cervical and Endometrial Cancers in Vitro and In Vivo, *Dissertations from the Faculty of Medicine—Uppsala*, vol. 1374, pp. 11-62, Jan. 2004.

Li, J., et al., (DN 103:65176) Catechol Formation of Fluoro- and Bromo-substituted Estradiols by Hamster Liver Microsomes. Evidence for Dehalogenation, *CAPLUS: Molecular Pharmacology*, vol. 27 (5), pp. 559-565, 1985.

Lichtenauer et al., Zur Behandlung des Prostata-Karzinoms, *Deutsches medizinisches Journal*, vol. 23, pp. 248-249, Jan. 1972.

Lien, W. et al., The blood supply of experimental liver metastases. II. A Microcirculatory study of the normal and tumor vessels of the liver with the use of perfused silicone rubber, *Surgery*, vol. 68 (2), pp. 334-340, Aug. 1970.

Limantsev et al., Effect of some estrogen structural analogs on the development of the mouse embyo, *Akush Jinekol.* (Chemical Abstracts 97:85606), vol. 6, pp. 55-56, 1982.

Lin et al., Interactions of Tubulin with Potent Natural and Synthetic Analogs of the Antimitotic Agent Combretastatin: A Structure-Activity Study, *Molecular Pharmacology*, vol. 34 (2), pp. 200-208, Aug. 1988.

Lin et al., A Comparative Study on the Effects of 2,3,7,8,-Tetrochlorodibenzo-*p*-Dioxin Polychlorinated Biphenyl126 and Estrogen in Human Bronchial Epithelial Cells, *Toxicology and Applied Pharmacology*, vol. 195, pp. 83-91, Jan. 1, 2004.

Lin et al., 2-Methoxyestradiol-Induced Caspace-3 Activation and Apoptosis Occurs Through $G_2/M$ Arrest Dependent and Independent Pathways in Gastric Carcinoma Cells, *Cancer*, vol. 92, pp. 500-509, Aug. 1, 2001.

Lin et al., Comparison of 2-Methoxyestradiol-Induced, Docetaxel-Induced, and Paclitaxel-Induced Apoptosis in Hepatoma Cells and Its Correlation with Reactive Oxygen Species, *Cancer*, vol. 89 (5), pp. 983-994, Sep. 1, 2000.

Lincoln et al., Conformation of Thiocolchicine and Two B-Ring-Modified Analogues Bound to Tubulin Studied with Optical Spectroscopy, *Biochemistry*, vol. 30 (5), pp. 1179-1187, Feb. 5, 1991.

Lippert et al., The effects of A-ring and D-ring metabolites of estradiol on the proliferation of vascular endothelial cells, *Life Sciences*, vol. 67, pp. 1653-1658, 2000.

Lippert et al., The Impact of Endogenous Estradiol Metabolites on Carcinogenesis, *Steroids*, vol. 65, pp. 357-369, Jan. 1, 2000.

Lis et al., 2-Methoxyestradiol inhibitsd proliferation of normal and neoplastic glial cells, and induces cell death, in vitro, *Cancer Letters*, vol. 213, pp. 57-65, Jan. 2004.

Liu et al., Total Synthesis of $(+-)-D^{9(12)}$-Capnellene, *Tetrahedron Letters*, vol. 26 (40), pp. 4847-4850, 1985.

Liu et al., Suppressive effects of 17b-estradiol on hepatic fibrosis in CC14-induced rat model, *World Journal of Gastroenterology*, vol. 10 (9), pp. 1-11, May 1, 2004.

Liu et al., Concentration-dependent mitogenic and antiproliferative actions of 2-methoxyestradiol in estrogen receptor-positive human breast cancer cells, *Steroid Biochemistry & Molecular Biology*, vol. 88, pp. 265-275, Jan. 1, 2004.

Liu et al., Selective Insensitivity of ZR-75-1 Human Breast Cancer Cells to 2- Methooxyestradiol: Evidence for Type II 17β-Hydroxyestradiol Dehydrogenase as the Underlynig Cause, *Cancer Research*, vol. 65 (13), pp. 5802-5811, Jul. 1, 2005.

Liu et al., Inhibitory action of ICI-182, 780, an estrogen receptor antagonist, on $BK_{Ca}$ channel activity in cultured endothelial cells of human coronary artery, *Biochemical Pharmacology*, vol. 66, pp. 2053-2063, Jan. 2003.

Locci et al., Angiogenesis: A New Diagnostic Aspect of Obstetric and Gynecologic Echography, *Journal of Perinatal Medicine*, vol. 21 (6), pp. 453-473, Jan. 1, 1993.

Loozen et al., An Approach to the Synthesis of 7.beta.-amino Estrogens, *Recl.: J.R. Neth.Chem. Soc.*, vol. 102 (10), pp. 433-437, 1983.

Lottering et al., Effects of the 17β-Estradiol Metabolites on Cell Cycle Events in MCF-7 Cells (Chemical Abstracts Doc. No: 117:245769, 1992), *Cancer Research*, vol. 52, pp. 5926-5932, Nov. 1, 1992.

Lottering et al., 17β-Estradiol Metabolites Affect Some Regulators of the MCF-7 Cell Cycle, *Cancer Letters*, vol. 110, pp. 181-186, 1996.

Lovely et al., 2-(Hydroxyalkyl)estradiols: Synthesis and Biological Evaluation, *Journal of Medicinal Chemistry*, vol. 39, pp. 1917-1923, 1996.

Lui et al., Male Predominance in Hepatocellular Carcinoma: New Insight and a Possible Therapeutic Alternative, *Medical Hypothesis*, vol. 55 (4), pp. 348-350, Jan. 1, 2000.

Luo et al., Effect of Components of Crown Ether Copper(I)Iodide Mixed Catalyst on Nucleophilic Substitution of Bromoestrogen (Abstract No. 195225), *Chemical Abstracts*, vol. 111 (21), pp. 818, col. 1, Nov. 20, 1989.

MacCarthy-Morrough et al., Differential Effects of Estrone and Estrone-3*O*-Sulfamate Derivatives on Mitotic Arrest, Apoptosis, and Microtubule Assembly in Human Breast Cancer Cells, *Cancer Research*, vol. 60, pp. 5441-5450, Oct. 1, 2000.

Macewen et al., 2-Methoxyestradiol (2ME2): In Vitro Apoptosis and Cell Cycle Inhibition and In Vivo Antitumor Activity in Canine Spontaneous Tumors, *American Association for Cancer Research—92nd Annual Meeting*, pp. Abstract #20, Mar. 24, 2001.

Mahadevan et al., Metastasis and Angiogenesis, *Acta Oncologica*, vol. 29 (1), pp. 97-103, Jan. 1, 1990.

Manfredi et al., Taxol: An Antimitotic Agent with a New Mechanism of Action, *Pharmacology & Therapeutics*, vol. 25 (1), pp. 83-125, 1984.

Mann et al., Choroidal Neovascularization with Granulomatous Inflammation in Ocular Histoplasmosis, Syndrome *American Journal of Ophthalmology*, vol. 130 (2), pp. 247-250, Aug. 1, 2000.

Maran et al., 2-Methoxyestradiol Induces Interferon Gene Expression and Apoptosis in Osteosarcoma Cells, *Bone*, vol. 30 (2), pp. 393-398, Feb. 2002.

Maro et al., Mechanism of Polar Body Formation in the Mouse Oocyte: An Interaction Between the Chromosomes, the Cytoskeleton and the Plasma Membrane, *Journal of Embryology and Experimental Morphology*, vol. 92, pp. 11-32, 1986.

Maro et al., Changes in Actin Distribution During Fertilization of the Mouse Egg, *Journal of Embryology and Experimental Morphology*, vol. 81, pp. 211-237, 1984.

Marti et al., Hypoxia-Induced Vascular Endothelial Growth Factor Expression Precedes Neovascularization after Cerebral Ischemia, *American Journal of Pathology*, vol. 156 (3), pp. 965-976, Mar. 1, 2000.

Matsunaga et al., Angiogenesis from the Eighth Cranial Nerve to Vestibular Schwannomas, *Acta Otolaryngology*, vol. 116 (1), pp. 52-58, Jan. 1, 1996.

Mayol et al., Ethynylestradiol-Induced Cell Proliferation in Rat Liver Involvement of Specific Populations of Hepatocytes, *Carcinogenesis*, vol. 13 (12), pp. 2381-2388, 1992.

Meikrantz et al., Apoptosis and the Cell Cycle, *Journal of Cellular Biochemistry*, vol. 58 (2), pp. 160-174, Jun. 1995.

Meza et al., Managing the Gastrointestinal Complications of AIDS, *Drug Therapy*, vol. 23 (11), pp. 74-83, Nov. 1993.

Michel et al., Inhibition of Synaptosomal High-Affinity Uptake of Dopamine and Serotonin by Estrogen Agonists and Antagonists, *Biochem. Pharmacol*, vol. 36 (19), pp. 3175-3180, 1987.

Miller et al., Synthesis and Structure-Activity Profiles of A-Homoestranes, the Estratropones, *Journal of Medicinal Chemistry*, vol. 40, pp. 3836-3841, 1997.

Miller, Thomas, Tubulin as a Therapeutic Target, *Dissertations Abstracts International*, vol. 5907B, p. 3454, 1998.

Mollendorff, W. Von, Wachstumsstorungen durch Geschlechtshormone, nach Untersuchungen an Gewebekulturen, pp. 187-202, Jun. 12, 1941.

Montgomery et al., Estrogen Effects on Tubulin Expression and Taxane Mediated Cytotoxicity in Prostate Cancer Cells, *The Prostate*, vol. 9999. pp. 1-10, Jan. 2005.

Mooberry, Susan, New insights into 2-methoxyestradiol, a promising antiangiogenic and antitumor agent, *Current Opinions in Oncology*, vol. 15, pp. 425-430, Nov. 2003.

Morgan et al., Calcium and Oestrogen Interactions upon the Rat Thymic Lymphocyte Plasma Membrane (Chemical Abstracts Doc. No: 85:172052, 1976), *Biochemical and Biophysical Research Communications*, vol. 72 (2), pp. 663-672, Sep. 20, 1976.

Morisaki et al., Steroids. L1. Aromatization reaction of the cross-conjugated dienone system by Zinc 9. *Chem. Pharm. Bull*, vol. 14 (8), pp. 866-872, 1966.

Mueck et al. Angiogenetic and Anti-Angiogenetic Effects of Estradiol and Its Metabolites. *Journal of Clinical and Basic Cardiology*, vol. 4 (2), pp. 153-155, 2001.

Mueck et al., Estrogen-dependent Neoplasia—What is the Significance of Estradiol Metabolites, *Zentralbi Gynakol*, vol. 125, pp. 458-466, Jan. 2003.

Mueck et al., Estradiol metabolism and malignant disease, *Maturitas*, vol. 43, pp. 1-10, Jan. 2002.

Mueck et al., Chemotherapy of breast cancer-additive anticancerogenic effects by 2-methoxyestradiol, *Life Sciences*, vol. 75, pp. 1205-1210, Jan. 2004.

Mukhopadhyay et al., Induction of Apoptosis in Human Lung Cancer Cells after Wild-Type p53 Activation by Methoxyestradiol, *Oncoaene*, vol. 14, pp. 379-384, 1997.

Mukhopadhyay et al., Two-dimensional gel analysis of apoptosis-specific p53 isoforms induced by 2-methoxyestradiol in human lung cancer cells, *Apoptosis*, vol. 3, pp. 421-430, Jan. 1998.

Mukundan et al., Liver Regeneration in Oral Contraceptive Treated Female Rats—Effects of Moderate Malnutrition (Chemical Abstracts Doc. No: 102:143342, 1984), *Hormone and Metabolic Research*, vol. 16 (12), pp. 641-645, Dec. 1984.

Naafs et al., Thalidomide Therapy An Open Trial, *International Journal of Dermatology*, vol. 24 (2), pp. 131-134, Mar. 1985.

Nakagawa-Yagi et al., The Endogenous Estrogen Metabolite 2-Methoxyestradiol Induces Apoptotic Neuronal Cell Death In Vitro, *Life Sciences*, vol. 58 (17), pp. 1461-1467, 1996.

Nakamura et al., Studies on the Total Synthesis of *dl*-Colchiceine. I. Synthesis of 3-Hydroxy-9, 10, 11-trimethoxy-1,2,3,4,6,7-hexahydro-5*H*-dibenzo[a,c] cycloheptatrien-5-one, *Chemical and Pharmaceutical Bulletin*, vol. 10, pp. 281-290, 1962.

Nambara et al., Studies on Steroid Conjugates. III. New Synthesis of 2-Methoxyestrogens, *Chem. Pharm. Bulletin*, vol. 18 (3), pp. 474-480, Mar. 1970.

Nambara et al., Microbial Transformation Products Derived from Steriods. I. Synthesis of 1,2- and 3-Dimethoxy-4-Methylestratrienes, *Chem. Pharm. Bull*, vol. 20 (2), pp. 336-342, 1972.

Nambara et al., Synthesis of 16β-Oxygenated Catechol Estrogen Methyl Ethers, New and Potential Metabolites, *Chemical & Pharmaceutical Bulletin*, vol. 23 (7), pp. 1613-1616, Jul. 1975.

Nambara, T., et al., DN 82:43650; Analytical Chemical Studies on Steroids. LXXIII. Synthesis of Epimeric 2-Hydroxy-16-Chlorestrong Monomethyl Ethers, *HCAPLUS—Chemical and Pharmaceutical Bulletin*, vol. 22 (10), pp. 2455-2457, 1974.

Napolitano et al., 11 Beta-Substituted Estradiol Derivatives. 2. Potential Carbon-11 and Iodine-Labeled Probes for the Estrogen Receptor, *Journal of Medicinal Chemistry*, vol. 38 (14), pp. 2774-2779, Jul. 7, 1995.

Nelimarkka et al., Decorin is Produced by Capillary Endothelial Cells in Inflammation-Associated Angiogenesis, *American Journal of Pathology*, vol. 158 (2), pp. 345-353, Feb. 1, 2001.

Nelson, J.D., Superior Limbic Keratoconjunctivitis (SLK), *Eye*, vol. 3 (Pt 2), pp. 180-189, Jan. 1, 1989.

Newkome et al., Synthesis of Simple Hydrazones of Carbonyl Compounds by an Exchange Reaction, *Journal of Oreanic Chemisty*, vol. 31, pp. 677-681, Mar. 1966.

Newman et al., Inhibition of In Vitro Angiogenesis by 2-Methoxy- and 2-Ethyl-Estrogen Sulfamates, *International Journal of Cancer*, vol. 109, pp. 533-540, Jan. 2004.

Nguyen et al., A Common Pharmacophore for a Diverse Set of Colchicine Site Inhibitors Using a Structure-Based Approach, *J. Med. Chem.*, vol. 48, pp. 6107-6116, Jan. 2005.

Nguyen, M. et al., Elevated Levels of the Angiogenic Peptide Basic Fibroblast Growth Factor in Urine of Bladder Cancer Patients, *Journal of the National Cancer Institute*, vol. 85 (3), pp. 241-242, Feb. 3, 1993.

Nishigaki et al., Anti-Proliferative Effect of 2-Methoxyestradiol on Cultured Smooth Muscle Cells from Rabbit Aorta, *Atherosclerosis*, vol. 113, pp. 167-170, 1995.

Numazawa et al., Efficient Synthesis of 2-Methoxy- and 4-Methoxy-Estrogens, *Journal of the Chemical Society*, pp. 533-534, Jan. 1, 1983.

Numazawa et al., Novel and Regiospecific Synthesis of 2-Amino Estrogens via Zincke Nitration, *Steroids*, vol. 41 (5), pp. 675-682, 1983.

Numazawa et al., Synthesis of 2-Methoxy- and 4-Methoxy-Estrogens with Halogen-Methoxy Exchange Reactions, *Journal of Chemical Research*, pp. 348-349, Jan. 1, 1985.

Ochs et al., Effect of Tumor Promoting Contraceptive Steroids on Growth and Drug Metabolizing Enzymes in Rat Liver, *Cancer Research*, vol. 46 (3), pp. 1224-1232, 1986.

Omar et al., Synthesis,Binding Affinities and Uterotrophic Activity of Some 2-Substituted Estradiol and Ring-A-Fused Pyrone Derivatives, *European Journal of Medicinal Chemistry*, vol. 29, pp. 25-32, 1994.

Oppolzer et al., 177. The Enantioselective Synthesis of (+)-Estradiol from 1,3-Dihydrobenzo[c] thiophene-2,2-dioxide by Successive Thermal $SO_2$-Extrusion and Cycloaddition Reactions, *Helvetica Chimica Acta*, vol. 63, pp. 1703-1705, 1980.

Pakala et al., Modulation of Endothelial Cell Proliferation by Retinoid x Receptor Agonists, *European Journal of Pharmacology*, vol. 385 (2/3), pp. 255-261, Sep. 1999.

Paller et al., Response to Anti-Angiogenic Therapies, *Journal of Investigative Dermatology*, vol. 5 (1), pp. 83-86, Dec. 1, 2000.

Paquette et al., Activation of matrix metalloproteinase-2 and -9 by 2- and 4-hydroxyestradiol, *The Journal of Steroid Biochemistry & Molecular Biology*, vol. 87, pp. 65-73, Jan. 2003.

Parthasarathy et al., Antioxidant: A New Role for RU-486 and Related Compounds, *Journal of Clinical Investigation*, vol. 94 (5), pp. 1990-1995, Nov. 1994.

Patz, A., Clinical and Experimental Studies on Retinal Neovascularization. XXXIX Edward Jackson Memorial Lecture. *American Journal of Ophthalmology*, vol. 94 (6), pp. 715-743, Dec. 1, 1982.

Paull et al., Identification of Novel Antimitotic Agents Acting at the Tubulin Level by Computer-assisted Evaluation of Differential Cytotoxicity Data, *Cancer Research*, vol. 52 (14), pp. 3892-3900, Jul. 15, 1992.

Pelicano et al., Inhibition of Mitochondrial Respiration, *The Journal of Biologicy Chemistry*, vol. 278 (39), pp. 37832-37839, Sep. 26, 2003.

Pellegrini et al., Revewi: Tubulin Function, Action of Antitubulin Drugs, and New Drug Development, *Cancer Investigation*, vol. 23, pp. 264-273, Jan. 1, 2005.

Penfold et al., Age-Related Macular Degeneration: Ultrastructural Studies of the Relationship of Leucocytes to Angiogenesis, *Graefes Archive for Clinical and Experimental Ophthalmology*, vol. 225 (1), pp. 70-76, Jan. 1, 1987.

Peng et al., Synthesis and Optical Properties of Novel Unsymmetrical Conjugated Dendrimers, *Journal of the American Chemical Society*, vol. 122, pp. 6619-6623, 2000.

Penn et al., The Effect of Angiostatic Steroid on Neovascularization in a Rat Model of Retinopathy of Prematurity, *Investigative Ophthalmology & Visual Science*, vol. 42 (1), pp. 283-290, Jan. 1, 2001.

Penn et al., Variable Oxygen Exposure Causes Preretinal Neovascularization in the Newborn Rat, *Investigative Ophthalmology & Visual Science*, vol. 34 (3), pp. 576-585, Mar. 1, 1993.

Perez-Stable, Carlos, 2-Methoxyestradiol and paclitaxel have similar effects on the cell cycle and induction of apoptosis in prostate cancer cells, *Cancer Lettters*, vol. 231, pp. 49-64, Jan. 2006.

Pert et al., Preparations of 2,4-disubstituted estradiols, *Australian Journal of Chemistry*, vol. 42 (3), pp. 421-432, 1989.

Peters et al., 17-Desoxy Estrogen Analogues, *Journal of Medicinal Chemistry*, vol. 32 (7), pp. 1642-1652, 1989.

Pfeiffer et al., Are Catechol Estrogens Obligatory Mediators of Estrogen Action in the Central Nervous System?I. Characterization of Pharmacological Probes with Different Receptor Binding Affinities and Catechol Estrogen Formation Rates, *Journal of Endocrinology*, vol. 110 (3), pp. 489-497, 1986.

Plum et al., Administration of a Liposomal FGF-2 Peptide Vaccine Leads to Abrogation of FGF-2-Mediated Angiogenesis and Tumor Development, *Vaccine*, vol. 19 (9-10), pp. 1294-1303, 2000.

Poli et al., Tumor Necrosis Factor α Functions in an Autocrine Manner in the Induction of Human Immunodeficiency Virus Expression, *Proceedings of the National Academy of Science USA*, vol. 87 (2), pp. 782-785, Jan. 1990.

Potvin et al., Mechanisms of Action of Antimalarials in Inflammation: Induction of Apoptosis in Human Endothelial Cells, *Journal of Immunobiology*, vol. 158 (4), pp. 1872-1879, Feb. 15, 1997.

Powell et al., Investigation and Treatment of Orogenital Ulceration; studies on a Possible Mode of Action of Action of Thalidomide, *British Journal of Dermatology*, vol. 113 Supp. 28, pp. 141-144, Jul. 1985.

Pribluda et al., 2-Methoxyestradiol—A Novel Endogenous Chemotherapeutic and Antiangiogenic Agent—Chapter 21, *The New Angiotherapy*, pp. 1-21, Nov. 2000.

Pribluda et al., 2-Methoxyestradiol: An endogenous antiangiogenic and antiproliferative drug candidate, *Cancer and Metastasis Reviews*, vol. 19, pp. 173-179, Jan. 1, 2000.

Purohit et al., The Effect of 2-Methoxyestrone-3-*O*-Sulphamate on the Growth of Breast Cancer Cells and Induced Mammary Tumours, *International Journal of Cancer*, vol. 85, pp. 584-589, Jan. 1, 2000.

Qadan et al., 2-Methoxyestadiol Induces G2/M Arrest and Apoptosis in Prostate Cancer, *Biochemical and Biophysical Research Communications*, vol. 285 (5), pp. 1259-1266, Jan. 2001.

Qanungo et al., 2-Methoxyestradiol induces mitochondria dependent apoptotic signaling in pancreatic cancer cells, *Oncogene*, vol. 21, pp. 4149-4157, Jan. 2002.

Rajkumar et al., Prevention of mammary carcinogenesis by short-term estrogen and progestin treatments, *Breast Cancer Research*, vol. 6 (1), pp. R31-R37, Nov. 11, 2003.

Ramanathan et al., Resistance to Paclitaxel is Proportional to Cellular Total Antioxidant Capacity, *Cancer Research*, vol. 65 (18), pp. 8455-8460, Sep. 15, 2005.

Ramirez et al., Estradiol, in the CNS, Targets Several Physiologically Relevant Membrane-Associated Proteins, *Brain Research Reviews*, vol. 37, pp. 141-152, Jan. 1, 2001.

Rao et al., Structural Specificity of Estrogens in the Induction of Mitotic Chromatid Non-Disjunction in Hela Cells, *Experimental Cell Research*, vol. 48, pp. 71-81, 1967.

Rao et al., A Novel, Two-Step Synthesis of 2-Methoxyestradiol, *Synthesis*, pp. 168-169, Mar. 1, 1977.

Rao et al., Synthesis and antimitotic activity of novel 2-methoxyestradiol analogs, *Steroids*, vol. 67, pp. 1079-1089, Jan. 2002.

Rao et al., A new, practical synthesis of 2-methoxyestradiols, *Steroids*, vol. 67, pp. 1065-1070, Jan. 2002.

Raobaikady et al., Inhibition of MCF-7 breast cancer cell proliferation and in vivo steroid sulphatase activity by 2-methoxyestradiol-bis-sulphamate, *The Journal of Steroid Biochemistry & Molecular Biology*, vol. 84, pp. 351-358, Jan. 2003.

Ravindra, R., Effect of Estradiol on the in vitro Assembly of Rat Brain Tubulin, *Journal of Indian Institute of Science*, vol. 64 (3), pp. 27-35, Mar. 1983.

Reddy et al. Ocular Complications Adult Rheumatoid Arthritis, *Rheumatology International*, vol. 16 (2), pp. 49-52, Jan. 1, 1996.

Reed et al., Aromatase Regulation and Breast Cancer, *Clinical Endocrinology*, vol. 54, pp. 563-571, Jan. 1, 2001.

Ribatti et al., Anti-Angiogenesis: A Multipurpose Therapeutic Tool?, *International Journal of Clinical & Laboratory Research*, vol. 23 (3), pp. 117-120, Jan. 1, 1993.

Riedel et al., Acute Vascular Responses to 17β-Estradiol in Postmenopausal Women With and Without Atherosclerosis, *Journal of the American College of Cardiology*, vol. Spec. Iss., pp. 380A, Mar. 13, 1994.

Riono et al., Scleritis: A Clinicopathologic Study of 55 Cases, *Ophthalmology*, vol. 106 (7), pp. 1328-1333, Jul. 1, 1999.

Robinson et al., Safety and Pharmacokinetics of Intravitreal 2-Methoxyestradiol Implants in Normal Rabbit and Pharmacodynamics in a Rat Model of Choroidal Neovascularization, *Experimental Eye Research*, vol. 74, pp. 309-317, pp. 309-317, Jan. 2002.

Robinson et al., Retinal Vein Occlusion, *American Family Physician*, vol. 45 (6), pp. 2661-2666, Jun. 1, 1992.

Rodi et al., Identification of Small Molecular Binding Sites within Proteins Using Phage Display Technology, *Combinatorial Chemistry & High Throughput Screening*, vol. 4, pp. 553-572, Jan. 1, 2001.

Romanelli et al., Ethyl-*p*-Dimethylaminophenylacetate, *Organic Synthesis*, vol. 5, pp. 552-554, Oct. 24, 1973.

Roth et al., Macular Translocation for Subfoveal Choroidal Neovascularization in Angioid Streaks, *American Journal of Ophthalmology*, vol. 131 (3), pp. 390-392, Mar. 1, 2001.

Rowsey et al., Radial Keratotomy: Preliminary Report of Complications, *Ophthalmic Surgery*, vol. 13 (1), pp. 27-35, Jan. 1, 1982.

Roy-Chaudhury et al., Venous Neointimal Hyperplasia in Polytetrafluoroethylene Dialysis Grafts, *Kidney International*, vol. 59 (6), pp. 2325-2334, Jan. 11, 2001.

Sakaguchi et al., Trehalose 6,6'-Dimycolate (Cord Factor) Enhances Neovascularization through Vascular Endothelial Growth Factor Production by Neutrophils and Macrophages, *Infection and Immunity*, vol. 68 (4), pp. 2043-2052, Apr. 1, 2000.

Sakakibara et al., Effects of Diethylstilbestrol and its Methl Ethers on Aneuploidy Induction and Microtubule Distribution in Chinese Hamster V79 cells, *Mutation Research*, vol. 263 (4), pp. 269-276, Aug. 1991.

Sakakibara, Kyoichi, 2-Hydroxy-1,3,5(10)-estratriene derivatives (XP: 002186126), *Chemical Abstracts*, vol. 60(1), Jan. 6, 1964.

Sanislo et al., Optic Nerve Head Neovascularization in a Patient with Inactive Cytomegalovirus Retinitis and Immune Recovery, *American Journal of Ophthalmology*, vol. 126 (2), pp. 318-320, Aug. 1, 1998.

Sato et al., Effect of Estradiol and Ethynylestradiol on Microtubule Distribution in Chinese Hamster V79 Cells, *Chemical and Pharmaceutical Bulletin*, vol. 40 (1), pp. 182-184, Jan. 1992.

Sato et al., Disruptive Effect of Diethylstilbestrol on Microtubules, *Gann*, vol. 75 (12), pp. 1046-1048, Dec. 1984.

Sato et al., Natural Estrogensn Induce Modulation of Microtubules in Chinese Hamster V79 Cells in Culture, *Horm. Carcinog. II. Proceedings Int. Symp.*, 2nd (1996). Meeting Date 1994, pp. 454-457, 1996.

Sato et al., Effects of Hormone Deprivation and 2-Methoxyestradiol Combination Therapy on Hormone-Dependent Prostate Cancer In Vivo, *Neoplasia*, vol. 7 (9), pp. 838-846, Sep. 2005.

Sawada et al., Colchicine-Like Effect of Diethylstilbestrol (DES) on Mammalian Cells in Vitro, *Mutation Research*, vol. 57, pp. 175-182, May 1978.

Schaub et al., Novel Agents that Promote Bone Regeneration, *Current Opinion in Biotechnology*, vol. 2 (6), pp. 868-871, Dec. 1, 1991.

Scherr et al., The Nonsteroidal Effects of Diethylstilbestrol: The Rationale for Androgen Deprivation Therapy without Estrogen Deprivation in the Treatment of Prostate Cancer, *The Journal of Urology*, vol. 170, pp. 1703-1708, Nov. 2003.

Schiff et al., Tubulin: A Target for Chemotherpeutic Agents, *Molecular Actions and Targets for Cancer Chemotherapeutic Agents*, pp. 483-507, Jan. 1, 1981.

Schumacher et al., The Physiological Estrogen Metabolite 2-Methoxyestradiol Reduces Tumor Growth and Induces Apoptosis in Human Solid Tumors, *Cancer Research Clinical Oncology*, vol. 127, pp. 405-410, 2001.

Schumacher et al., 2-Methoxyestradiol induces p53 independent apoptosis and inhibits growth of lung metastases of pancreatic cancer (English summary p. 52), *Langenbecks Arch Chir 1*, vol. 1, pp. 49-52, Jan. 1998.

Seeger et al., Different effects of estradiol and various antiestrogens on TNF-60 -induced changes of biochemical markers for growth and invasion of human breast cancer cells, *Life Sciences*, vol. XX, pp. 1-5, Jan. 2005.

Seegers et al., Cyclic-AMP and Cyclic-GMP Production in MCF-7 Cells Exposed to Estradiol-17 Beta, Catecholestrogens and Methoxy-Estrogens in MCF-7 Cells, *Joint MCI-1st Symposium. Third 1st International Symposium. Biology and Therapy*, Sep. 25, 1989.

Seegers et al., The Mammalian Metabolite, 2-methoxyestradiol, Affects P53 Levels and Apoptosis Induction in Transformed Cells but Not in Normal Cells, *Journal of Steroid Biochemistry and Molecular Biology*, vol. 62 (4), pp. 253-267, Jul. 1997.

Seegers, J.C. et al., The Cytotoxic Effects of Estradiol-17β, Catecholestradiols and Methoxyestradiols on Dividing MCF-7 and HeLa Cells, *Journal of Steroid Biochemistry*, vol. 32 (6), pp. 797-809, Jun. 1989.

Seng et al., Use of a monoclonal antibody specific for activated endothelial cells to quantitate angiogenesis in vivo in zebrafish after drug treatment, *Angiogenesis*, vol. 7, pp. 243-253, Jan. 2004.

Servold, S.A., Growth Factor Impact on Wound Healing, *Clinics in Podiatric Medicine and Surgery*, vol. 8 (4), pp. 937-953, Oct. 1, 1991.

Shah et al., (+/-)-(N-alkylamino)benzazepine Analogs: Novel Dopamine D1 Receptor Antagonists, *Journal of Medicinal Chemistry*, vol. 38 (21), pp. 4284-4293, Oct. 13, 1995.

Shah et al., Monocrotaline pyrrole-induced endothelial cell megalocytosis involves a Golgi blockage mechanism, *Am. J. Physiol. Cell Physiol.* vol. 288, pp. C850-C862, Nov. 23, 2004.

Shang et al., 2-Methoxyestradiol, an Endogenous Estradiol Metabolite, Differentially Inhibits Granulosa and Endothelial Cell Mitosis: A Potential Follicular Antiangiogenic Regulator, *Bilogy of Reproduction*, vol. 65, pp. 622-627, Jan. 1, 2001.

Sharp et al., Diethylstilboestrol: the Binding and Effects of Diethylstilboestrol upon the Polymerisation and Depolymerisation of Purified Microtubule Protein in vitro, *Carcinogenesis*, vol. 6 (6), pp. 865-871, Jun. 1985.

Sheela et al., Angiogenic and Invasive Properties of Neurofibroma Schwann Cells, *Joumal of Cell Biology*, vol. 111 (2), pp. 645-653, Aug. 1, 1990.

Shi et al., Encapsulation of Submicrometer-Sized 2-Methoxyestradiol Crystals into Polymer Multilayer Capsules for Biological Applications, *Molecular Pharmaceutics*, vol. 3 (2), pp. 144-151, 2006.

Shim et al., Hydrazinocurcumin, A Novel Synthetic Curcumin Derivative, Is a Potent Inhibitor of Endothelial Cell Proliferation, *Caplus: Bioorganic & Medicinal Chemistry*, vol. 10 (8), pp. 2439-2444, 2002.

Shimada et al., The Molecular Mechanism of Sensitization to Fas-Mediated Apoptosis by 2-Methoxyestradiol in PC3 Prostate Cancer Cells, *Molecular Carcinogenesis*, vol. 39, pp. 1-9, Jan. 1, 2004.

Shimada et al., Roles of p38- and c-jun NH2-terminal kinase-mediated pathways in 2-methoxyestradiol-induced p53 induction and apoptosis, *Carcinogenesis*, vol. 24 (6), pp. 1067-1075, Jan. 2003.

Shishkina et al., Synthesis and Properties of Condensed Heterocyclic Derivatives of Estra-4, 9-dien-17.beta.-ol-3-one, vol. 8 (1), pp. 7-11, 1974.

Shweiki et al., Patterns of Expression of Vascular Endothelial Growth Factor (VEGF) and VEGF Receptors in Mice Suggest a Role in Hormonally Regulated Angiogenesis, *Journal of Clinical Investigation*, vol. 91 (5), pp. 2235-2243, May 1, 1993.

Sibonga et al., Evidence that 2-methoxyestradiol suppresses proliferation and accelerates apoptosis in normal rat growth plate chondrocytes, *Journal of Cancer Research and Clinical Oncology*, vol. 128, pp. 477-483, Jan. 2002.

Sidky et al., Inhibition of Angiogenesis by Interferons: Effects on Tumor- and Lymphocyte-induced Vascular Responses, *Cancer Research*, vol. 47, pp. 5155-5161, Oct. 1, 1987.

Sidor et al., The Potential and Suitability of 2-Methoxyestradiol in Cancer Therapy, *Clinical Cancer Research*, vol. 11 (16), pp. 6094-6096, Aug. 15, 2005.

Simon, M., General Concepts of Angiogenesis, pp. 1-6, Apr. 17, 2000.

Singh et al., Inhibition of Deoxyglucose Uptake in MCF-7 Breast Cancer Cells by 2-Methoxyestrone and 2-Methoxyestrone-3-O-sulfamate, *Molecular and Cellular Endocrinology*, vol. 160 (1-2), pp. 61-66, 2000.

Singhal et al., Novel Therapies in Multiple Myeloma, *International Journal of Hematology*, vol. 77, pp. 226-231, Jan. 9, 2003.

Siracusa et al., The Effect of Microtubule- and Microfilament-disrupting Drugs on Preimplantation Mouse Embryos, *Jouranl of Embryology and Experimental Morphology*, vol. 60, pp. 71-82, Dec. 1980.

Sowka et al., Phlyctenulosis, *Handbook of Ocular Disease Management*, Jan. 1, 2000.

Spicer et al., Catecholestrogens Inhibit Proliferation and DNA Synthesis of Porcine Granulosa Cells in Vitro: Comparison and Estradiol, 5α-dihydrotestosterone, Gonadotropins and Catecholamines (Chemical Abstract Doc. No. 111:50609, 1989), *Molecular and Cellular Endocrinology*, vol. 64, pp. 119-126, 1989.

Spink et al., SULT1A1 Catalyzes 2-Methoxyestradiol Sulfonation in MCF-7 Breast Cancer Cells, *Carcinogenesis*, vol. 21 (11), pp. 1947-1957, Jan. 1, 2000.

Spyriounis et al., Copper (II) complex of an estradiol derivative with potent antiinflammatory properties, *Arch. Pharm.*, vol. 324 (9), pp. 533-536, 1991.

Srivastava, A. et al., The Prognostic Significance of Tumor Vascularity in Intermediate-Thickness (0.76-4.0 mm Thick) Skin Melanoma, *American Journal of Pathology*, vol. 133 (2), pp. 419-424, Nov. 1, 1988.

Stafford et al., Colchicine and 2-methoxyestradiol Inhibit Human Angiogenesis, *Journal of Surgical Research*, vol. 125, pp. 104-108, Jan. 1, 2005.

Staples et al., Structural Requirements for Steroid Inhibition of Sheep Lymphocyte Mitogenesis in vitro, *Steroids*, vol. 44 (5), pp. 419-433, Nov. 1984.

Starkov et al., Mono- and Dialkylation of Guaiacol by Olefins on KU-2 Cation Exchanger, *Zhumal Prikladnoi Khimii*, vol. 41 (3), pp. 688-690, 1968.

Sternlicht et al., Colchicine Inhibition of Microtubule Assembly via Copolymer Formation, *The Journal of Biological Chemistry*, vol. 254 (20), pp. 10540-10550, Oct. 25, 1979.

Stiffey-Wilusz et al., An ex vivo Angiogenesis Assay Utilizing Commercial Porcine Carotid Artery: Modification of the Rat Aortic Ring Assay, *Angiogenesis*, vol. 4, pp. 3-9, Jan. 1, 2001.

Strizzi et al., Vascular Endothelial Growth Factor is an Autocrine Growth Factor in Human Malignant Mesothelioma, *Journal of Pathology*, vol. 193 (4), pp. 468-475, Apr. 1, 2001.

Subbaramaiah et al., Microtubule-Interfering Agents Stimulate the Transcription of Cyclooxygenase-2, *The Journal of Biological Chemistry*, vol. 275 (20), pp. 14838-14845, May 19, 2000.

Sudhoff et al., Angiogenesis and Angiogenic Growth Factors in Middle Ear Cholesteatoma, *American Journal of Otolaryngology*, vol. 21 (6), pp. 793-798, Nov. 1, 2000.

Sun et al., Antitumor Agents. 139. Synthesis and Biological Evaluation of Thiocolchicine Analogs 5,6-Dihydro -6(S)-(acyloxy)-and 5,6-Dihydro-6(S)-[(aroyloxy) methyl}-1,2,3- trimethoxy-9-(methylthio)-8H-cyclohepta[α]naphthalen-8-ones as Novel Cvtotoxic and Antimitotic Agents, *Journal of Medicinal Chemistry*, vol. 36 (5), pp. 544-551, Mar. 5, 1993.

Sun et al., In Vivo and in Vitro Characteristics of Interleukin 6-Transfeected B16 Melanoma Cells, *Cancer Research*, vol. 52, pp. 5412-5415, Oct. 1, 1992.

Sunagawa et al., Synthesis of Colchicine; Synthesis of dl-Demethyoxydeoxy-hexahydrocolchicine, *Chemical & Pharmaceutical Bulletin*, vol. 9, pp. 81-83, 1961.

Sutherland et al., 2-Methoxyestradiol Is an Estrogen Receptor Agonist That Supports Tumor Growth in Murine Xenograft Models of Breast Cancer, *Clinical Cancer Research*, vol. 11, pp. 1722-1732, Mar. 1, 2005.

Suzuki et al., Growth inhibition of multi-drug-resistant breast cancer cells by 2-methoxyesradiol—bis-sulphamate and 2-ethyloestradiol-bis-sulphamate, *The Journal of Steroid Biochemistry & Molecular Biology*, vol. 84, pp. 269-278, Jan. 2003.

Sweeney et al., A Phase II Multicenter, Randomized, Double-Blind, Safety Trial Assessing the Pharmacokinetics, Pharmacodynamics and Efficacy of Oral 2-Methoxyestradiol Capsules in Hormone-Refractory Prostate Cancer, *Clinical Cancer Research*, vol. 11 (18), pp. 6625-6633, Sep. 15, 2005.

Sweeney et al., The Antiangiogenic Property of Docetaxel Is Synergistic with a Recombinant Humanized Monoclonal Antibody Against Vascular Endothelial Growth Factor or 2-Methoxyestradiol but Antagonized by Endothelial Growth Factor, *Cancer Research*, vol. 61, pp. 3369-3372, Apr. 15, 2001.

Tabbara, K.F., Disruption of the Choroidoretinal Interface by Toxoplasma, *Eye*, vol. 4 (Part 2), pp. 366-373, Jan. 1, 1990.

Takahashi et al., Effects of estrogens and metabolites on endometrial carcinogenesis in young adult mice initiated with N-ethyl-N'-nitro-N-nitrosoguanidine, *Cancer Letters*, vol. 211, pp. 1-9, Jan. 2004.

Takanashi et al., Metabolism of [6,7-$^3$H, $^{35}$S] estradiol 17 sulfate in rats, *Steroids*, vol. 68, pp. 383-392, Jan. 2003.

Takanashi et al., Comparison of ex vivo Inhibitory Effect Between 2-Hydroxyestradiol and Its 17-Sulfate on Rat Hepatic Microsomal Lipid Peroxidation, *Lipids*, vol. 38 (8), pp. 847-854, Jan. 2003.

Takata et al., 2-Methoxyestradiol Enhances p53 Protein Trasduction Therapy-Associated Inhibition of the Proliferation of Oral Cancer Cells through the Suppression of NF-B Activity, *Acta Medica Okayama*, vol. 58 (4), pp. 181-187, Jan. 2004.

Talarico et al., Protection of Mice Against Tumor Growth by Immunization with an Oncogene-Encoded Growth Factor, *Proceedings of the National Academy of Science USA*, vol. 87, pp. 4222-4225, Jun. 1990.

Taylor, S. et al., Protamine is an Inhibitor of Angiogenesis, *Nature*, vol. 297, pp. 307-312, May 27, 1982.

Teranishi, M. et al., Methylation of Catechol Estrogen with Diazomethane, *Chemical and Pharmaceutical Bulletin*, vol. 31 (9), pp. 3309-3314, Sep. 1983.

Timar et al., Angiogenesis-Dependent Diseases and Angiogenesis Therapy, *Patholoy and Oncology Research*, vol. 7 (2), pp. 85-94, Jan. 1, 2001.

Tishler et al., Microtubule-Active Drugs Taxol, Vinblastine, and Nocodazole Increase the Levels of Transcriptionally Active p53, *Cancer Research*, vol. 55, pp. 6021-6025, Dec. 15, 1995.

Tofovic et al., Estradiol Metabolites Attenuate Renal and Cardiovascular Injury Induced by Chronic Nitric Oxide Synthase Inhibition, *Journal of Cardiovascular Pharmacology*, vol. 46 (1), pp. 25-35, Jul. 2005.

Tofovic et al., Estradiol Metabolites Attenuate Monocrotaline-Induced Pulmonary Hypertension in Rats, *Journal of Cardiovascular Pharmacology*, vol. 46 (4), pp. 430-437, Oct. 2005.

Tremblay et al., A Convenient Synthetic Method for Alpha-Alkylation of Steroidal 17-Ketone: Preparation of 16β-(THPO-Heptyl)-Estradiol, *Synthetic Communications*, vol. 25 (16), pp. 2483-2495, 1995.

Tremblay et al., Synthesis of 16-(Bromoalkyl)-Estradiols Having Inhibitory Effect on Human Placental Estradiol 17β-Hydroxysteroid Dehydrogenase (17β-HSD Type 1) *Bioorganic & Medicinal Chemistry*, vol. 3 (5), pp. 505-523, 1995.

Tsutsui et al., Comparison of Human Versus Syrian Hamster Cells in Culture for Induction of Mitotic Inhibition, Binucleation and Multinucleation, Following Treatment with Four Aneuploidogens, *Toxicology in Vitro*, vol. 4 (1), pp. 75-84, 1990.

Tsutsui et al., Induction of Mammalian Cell Transformation and Genotoxicity by 2-Methoxyestradiol, an Endogenous Metabolite of Estrogen, *Carcinogenesis*, vol. 21 (4), pp. 735-740, Jan. 1, 2000.

Tuder et al., The Pathobiology of Pulmonary Hypertension. Endothelium, *Clinicals in Chest Medicine*, vol. 22 (3), pp. 405-418, Sep. 1, 2001.

Turner et al., 2-Methoxyestradiol Inhibits Longitudinal Bone Growth in Normal Female Rats, *Calcified Tissue International*, vol. 66, pp. 465-469, Jan. 1, 2000.

Urakawa et al., Examination of a modified cell cycle synchronization method and bovine nuclear transfer using synchronized early G1 phase fibroblast cells, *Theriogenology*, vol. 62, pp. 714-728, Jan. 2004.

Utne et al., The Synthesis of 2- and 4-Fluoroestradiol *Journal of Organic Chemistry*, vol. 33 (6), pp. 2469-2473, Jun. 1968.

Van Der Eerden et al., Evidence for genomic and nongenomic actions of estrogen in growth plate regulation in female and male rats at the onset of sexual maturation, *Journal of Endocrinology*, vol. 175, pp. 277-288, Jan. 2002.

Van Duursen et al., Effects of several dioxin-like compounds on estrogen metabolism in the malignant MCF-7 and nontumorigenic MCF-10A human mammary epithelial cell lines, *Toxicology and Applied Pharmacology*, vol. 190, pp. 241-250, Jan. 2003.

Van Geerestein et al., Structure of 11.beta.-(4-(dimethylamino)phenyl)-17.beta.-hydroxy-17. alpha.-(2-propenyl) estra-4,9-dien-3-one (Identifier only), *Acta Crystallogr.. Sect, C: Cryst. Struct. Commun.*, vol. C43 (2), pp. 319-322, 1987.

Van Tamelen et al., The Synthesis of Colchicine, *Tetrahedron*, vol. 14 (1/2), pp. 8-34, Sep. 1961.

Verdier-Pinard et al., A Steroid Derivative with Paclitaxel-Like Effects on Tubulin Polymerization, *Molecular Pharmacology*, vol. 57, pp. 568-575, Jan. 1, 2000.

Verma et al., Adjuvant Effects of Liposomes Containing Lipid A: Enhancement of Liposomal Antigen Presentation and Recruitment of Macrophages, *Infection and Immunity*, vol. 60 (6), pp. 2438-2444, Jun. 1, 1992.

Vicente et al., In Vitro Activity of Thalidomide Against Mycobacterium avium Complex, *Archives of Internal Medicine*, vol. 153 (4), pp. 534, Feb. 22, 1993.

Viggiano et al., Trigeminal pain transmission requires reactive oxygen species production, *Brain Research*, vol. 1050, pp. 72-78, Jan. 1, 2005.

Walsh et al., Angiogenesis in the Pathogenesis of Inflammatory Joint and Lung Diseases, *Arthritis Research*, vol. 3 (3), pp. 147-153, Jan. 1, 2001.

Wang et al., Photoaffinity Labeling of Human Placental Estradiol 17.beta.-dehydrogenase with 2- and 4-azidoestrone, 2- and 4-azidoestradiol *Shengwu Huaxue Zazhi*, vol. 8 (6), pp. 715-718, 1992.

Wang et al., Synthesis of B-Ring Homologated Estradiol Analogues that Modulate Tubulin Polymerization and Microtubule Stability, *Journal of Medicinal Chemistry*, vol. 43, pp. 2419-2429, 2000.

Wang et al., A Simple Quantitative Method for Evaluation of Angiogenesis Activity, *ASSAY and Drug Develooment Technologies*, vol. 2 (1), pp. 31-38, Jan. 2004.

Wang et al., 2-Methoxyestradiol, an Endogenous Estrogen Metabolite, Induces Thyroid Cell Apoptosis, *Molecular and Cellular Endocrinology*, vol. 165, pp. 163-172, Jan. 1, 2000.

Wang, Z. et al., An Optimized Synthesis of 2-Methoxyestradiol, a Naturally Occurring Human Metabolite with Anticancer Activity, *Synth. Commun*, vol. 28 (23), pp. 4431-4437, 1998.

Watson, P.G. Management of Mooren's Ulceration, *Eye*, vol. 11 (Pt 3), pp. 349-356, Jan. 1, 1997.

Webb et al., Cell-Surface Expression and Purification of Human CD-4 Produced in Baculovirus-Infected Insect Cells, *Proceedings of the National Academy of Science (USA)*, vol. 86 (20), pp. 7731-7735, Oct. 1, 1989.

Weidner, N. et al., Tumor angiogenesis: A New Significant and Independent Prognostic Indicator in Early-Stage Breast Carcinoma, *Journal of the National Cancer Institute*, vol. 84, pp. 1875-1887, Dec. 16, 1992.

Weidner, N. et al., Tumor Angiogenesis Correlates with Metastasis in Invasive Prostate Carcinoma, *American Journal of Pathology*, vol. 143 (2), pp. 401-409, Aug. 1, 1993.

Weidner, N. et al., Tumor Angiogenesis and Metastasis—Correlation in Invasive Breast Carcinoma, *New England Journal of Medicine*, vol. 324 (1), pp. 1-8, Jan. 3, 1991.

Welsch et al., Staphylostatic Activity of Some New Diphenols, Napthols, and Chalcones, *Experientia*, vol. 11, pp. 350-351, 1955.

Wheeler et al., Mitotic Inhibition and Aneuploidy Induction by Naturally Occurring and Synthetic Estrogens in Chinese Hamster Cells in Vitro, *Mutation Research*, vol. 171, pp. 31-41, Jul. 1986.

Wheeler et al., Mitotic Inhibition and Chromosome Displacement Induced by Estradiol in Chinese Hamster Cells (Chemical Abstracts Doc. No. 105:54822, 1986) *Cell Motility and the Cytoskeleton*, vol. 7 (3), pp. 235-247, 1987.

White et al., Treatment of Pulmonary Hemangiomatosis with Recombinant Interferon Alfa-2a, *The New England Journal of Medicine*, vol. 32 (18), pp. 1197-1200, May 4, 1989.

Wiedemann, P., Growth Factors in Retinal Disease: Proliferative Vitreoretinopathy, Proliferative Diabetic Retinopathy, and Retinal Degeneration, *Survey of Ophthalmology*, vol. 36 (5), pp. 373-384, Mar. 1, 1992.

Wiese et al., Induction of the Estrogen Specific Mitogenic Response of MCF-7 Cells by Selected Analogues of Estradiol-17 β. A 3D QSAR Study, *Journal of Medicinal Chemistry*, vol. 40, pp. 3659-3669, 1997.

Wood et al., 2-MeOE2bisMATE induces caspase-despendent apoptosis in CAL51 breast cancer cells and overcomes resistance to TRAIL via cooperative activation of caspases, *Apoptosis*, vol. 9, pp. 323-332, Jan. 2004.

Wurtz et al., Three-Dimensional Models of Estrogen Receptor Ligand Binding Domain Complexes, Based on Related Crystal Structures and Mutational and Structure—Activity Relationship Data, *Journal of Medicinal Chemistry*, vol. 41, pp. 1803-1814, 1998.

Xiao et al., Effects of Estradiol and Its Metabolites on Glomerular Endothelial Nitric Oxide Synthesis and Mesangial Cell Growth, *Hypertension*, vol. 37 (part 2), pp. 645-650, Feb. 1, 2001.

Yang et al., Consitutively active FOX04 inhibits Akt activity, regulates p27 Kip1 stability, and suppresses HER2-medicated tumorigenicity, *Oncoeene*, vol. 24, pp. 1924-1935, Jan. 1, 2005.

Yang, Ning-Sun, Gene Transfer into Mammalian Somatic Cells In Vivo, *Critical Reviews in Biotechnology*, vol. 12 (4), pp. 335-356, 1992.

Yasuda et al., Accelerated differentiation in seminiferous tubules of fetal mice prenatally exposed to ethinyl estradiol, *Anat. Embryol. (Berl.)*, vol. 174 (3), pp. 289-299, 1986.

Yazaki et al., Inhibition of Angiogenesis and Growth of Human Non-Malignant and Malignant Meningiomas by TNP-470, *Journal of Neurooncology*, vol. 23 (1), pp. 23-29, Jan. 1, 1995.

Yue et al., 2-Methoxyestradiol, and Endogenous Estrogen Metabolite, Induces Apoptosis in Endothelial Cells and Inhibits Angiogenesis: Possible for Stress-Activated Protein Kinase Signaling Pathway and Fas Expression, *Molecular Pharmacology*, vol. 51, pp. 951-962, 1997.

Zacharia et al., 2-Hydroxyestradiol Is a Prodrug of 2-Methoxyestradiol, *Journal for Pharmacology and Experimental Therapeutics*, vol. 62505, pp. 1-25, Feb. 10, 2004.

Zacharia et al., Methylation of 2-Hydroxyestradiol in Isolated Organs, *Hypertension*, vol. 42, pp. 82-87, Jan. 2003.

Zacharia et al., Methoxyestradiols Mediate the Antimitogenic Effects of 17β-Estradiol, *Circulation*, vol. 108, pp. 2974-2978, Dec. 16, 2003.

Zacharia et al., Catecholamines Abrogate Antimitogenic Effects of 2-Hydroxyestradiol on Human Aortic Vascular Smooth Muscle Cells, *Anteriosclerosis. Thrombosis and Vascular Biology*, vol. 21, pp. 1745-1750, Nov. 1, 2001.

Zacharia et al., Increased 2-Methoxyestradiol Production in Human Coronary Versus Aortic Vascular Cells, *Hypertension*, vol. 37 (part 2), pp. 658-662, Feb. 1, 2001.

Zhang et al., Detection of 1,2,4-benzenetriol induced aneuploidy and microtubule disruption by flourescence in situ hybridization and immunocytochemistry, *Mutation Research*, vol. 320, pp. 315-327, 1994.

Zhang et al., Tumor suppressor ARF inhibits HER-2/neu-mediated oncogenic growth, *Oncogene*, vol. 23, pp. 7132-7143, Jan. 2004.

Zheng et al., Control of Stromal Keratitis by Inhibition of Neovascularization, *American Journal of Pathology*, vol. 159 (3), pp. 1021-1029, Sep. 1, 2001.

Zhou et al., 2-Methoxyestradiol induces cell cycle arrest and apoptosis of nasopharyngeal carcinoma cells, *Acta Pharmacologica Sinica*, vol. 25 (11), pp. 1515-1520, Nov. 2004.

Zhu et al., NADPH-dependent metabolism of 17B-estradiol and estrone to polar and nonpolar metabolites by human tissues and cytochrome P450 isoforms, *Steroids*, vol. 70, pp. 225-244, Jan. 1, 2005.

Zoubine et al., 2-Methoxyestradiol-Induced Growth Suppresion and Lethality in Estrogen-Responsive MCF-7 Cells May Be Mediated by Down Regulation of p34cdc2 and Cyclin B1 Expression, *International Journal of Oncology*, vol. 15 (4), pp. 639-646, Oct. 1999.

EPO Search, EPO Search Report Report filed in 05016659.4 dated Dec. 20, 2005, *EPO Search Report*, pp. 1-7.

PCT Search, PCT Search Report—Application No. PCT/US05/42944, *International Search Report Report*, pp. 1-5, Aug. 24, 2006.

PCT Search, PCT Search Report—Cited in PCT/US06/44152, *International Search Report*, pp. 1-4, Feb. 1, 2008.

PCT Search, PCT Search Report—PCT/US07/07007, *PCT Search Report*, pp. 1-6, Jul. 3, 2008.

Riedel et al., XP009057873; Abstract No. 952-132: Acute Vascular Responses to 17β-Estradiol in Postmenopausal Women with and without Atherosclerosis, *Journal of the American College of Cardiology*, pp. 380A, Mar. 13, 1994.

Office Action cited in U.S. Appl. No. 12/262,318 *USPTO Office Action*, pp. 1-8, Sep. 15, 2010.

Abe et al., Drug Therapy of Rheumatoid Arthritis, *Japanese Journal of Clinical Immunology* vol. 22 (2), pp. 35-42, Feb. 2, 2012.

\* cited by examiner

Figure 6

| Treatment Group | Total Osteoclast Numbers | Articular cartilage area without proteoglycan staining (%) | Damaged articular cartilage surface (%) | Thickness of total articular cartilage area (µM) |
|---|---|---|---|---|
| Vehicle Control | 33.9 | 17.23 | 47.35 | 26.06 |
| 2ME2 1mg/kg | 21.9 | 11.21 | 37.07 | 27.55 |
| 2ME2 10 mg/kg | 5.7 | 6.71 | 27.91 | 27.34 |
| 2ME2 100 mg/kg | 0 | 0.18 | 0 | 32.64 |

$p<0.05$

DISEASE MODIFYING ANTI-ARTHRITIC ACTIVITY OF 2-METHOXYESTRADIOL

CROSS-REFERENCE TO RELATED APPLICATIONS

The present application claims the benefit of U.S. Provisional Patent Application Ser. No. 60/784,206, filed Mar. 20, 2006, which is incorporated herein by reference in its entirety.

FIELD OF THE INVENTION

The present invention relates generally to compositions comprising anti-angiogenic agents in combination with anti-rheumatic agents and to methods of using the same. More specifically, the present invention relates to compositions comprising 2-methoxyestradiol, and derivatives thereof, in combination with anti-rheumatic agents. More particularly, the present invention relates to methods of treating rheumatoid arthritis and related rheumatic diseases by administering 2-methoxyestradiol, and derivatives thereof, in combination with one or more anti-rheumatic agents.

BACKGROUND OF THE INVENTION

Rheumatic diseases are characterized by inflammation and loss of function in one or more connecting or supporting structures of the body. Those structures especially affected are joints, tendons, ligaments, bones and muscles and in some cases internal organs. Some rheumatic diseases are classified as connective tissue disorders and include osteoarthritis, fibromyalgia, spondyloarthropathies, gout, polymyositis, bursitis and tendonitis. Other rheumatic diseases are classified as automimmune diseases including rheumatoid arthritis, systemic lupus erythematosus, polymyalgia rheumatica, scleroderma, and psoriatic arthritis. An estimated 45 million people in the United States have arthritis or other rheumatic conditions and rheumatic diseases are the leading cause of disability among adults age 65 and older. While the pathogenesis of the diseases may vary, their characteristic inflammatory symptoms often share common inflammatory mediators.

Rheumatoid arthritis (RA) is a rheumatic disease characterized by persistent synovial tissue inflammation. In time, this persistent inflammation can lead to bone erosion, destruction of cartilage, and complete loss of joint integrity. Eventually, multiple organs may be affected (Rindfleish et al. *American Family Physician* (2005), 72(6):103746). Joint damage is initiated by proliferation of synovial macrophages and fibroblasts after a triggering incident, possibly autoimmune or infectious. This is followed by infiltration of the perivascular regions by lymphocytes and endothelial cell proliferation. Over time, inflamed synovial tissue begins to grow irregularly, forming invasive pannus tissue. The pannus invades and destroys cartilage and bone. Multiple cytokines, interleukins, proteinases, and growth factors are released causing further joint destruction and the development of systemic conditions (Ruddy et al. eds. *Kelly's Textbook of Rheumatology*. 7$^{th}$ ed. Philadelphia: W.B. Saunders, 2005:996-1042).

The symptoms of rheumatoid arthritis present as pain and stiffness in multiple joints. Symptoms can emerge over weeks and are often accompanied by anorexia, weakness, or fatigue. Joints most commonly affected are those with the highest ratio of synovium to articular cartilage, including the wrists and the proximal interphalangeal and metacarpophalangeal joints (Ruddy et al. eds. *Kelly's Textbook of Rheumatology* 7$^{th}$ ed. Philadelphia: W.B. Saunders, 2005:996-1042). Destruction of joints can begin within a few weeks of symptom onset. Early diagnosis is imperative as early treatment is effective in slowing disease progression. However, there are currently no diagnostic tests that can conclusively confirm rheumatoid arthritis.

The management of rheumatoid arthritis typically consists of medication and non-medication based treatments. Treatments aimed at reversing the course of the disease have so far been largely unsuccessful. Instead, therapeutic goals typically focus on preservation of function and quality of life, minimization of pain and inflammation, joint protection, and control of systemic complications (Harris, (2005) and American College of Rheumatology Subcommittee on Rheumatoid Arthritis Guidelines, *Arthritis Rheum* (2002), 46:328-46). A typical treatment regimen includes administration of nonsteroidal anti-inflammatory drugs (NSAIDs) for control of pain, with selective use of oral and intra-articular glucocorticosteroids, and initiation of one or more disease-modifying anti-rheumatic drugs (DMARDs). DMARDs commonly used include methotrexate, hydroxychloroquine, sulfasalazine, and leflunomide. In a recent reversal of therapeutic paradigms, early and aggressive treatment with one or more DMARDs is now favored. While this more intensive regime has shown promise when treated early, only a fraction of patients achieve the ideal goal of halted progression and/or elimination of clinical activity (Machold et al., *Arthritis Research & Therapy* (2006), 8:1-6). A number of new biologics are also available for treating rheumatoid arthritis including infliximab (Remicade®), a chimeric tumor necrosis factor alpha (TNF-α) specific antibody; etanercept (Enbrel®), a soluble dimerized human p72 receptor/Fc fusion protein that competitively binds TNF-α; and anakinra, an interleukin-1 receptor blocker. While this new class of anti-rheumatic drugs has shown promise as a substitute or complementary form of treatment, infectious complications have been observed following treatment (Imaizumi et al., *Intern. Med.* (2006), 48(10):685-88).

There is an increasing appreciation for the role that angiogenesis plays in RA initiation and progression (Koch, *Ann Rheum Dis* (2000), 59(Suppl. I):i65-i71 and Veale et al., *Best Practice & Research Clinical Rheumatology* (2006), 20(5): 941-47). Chronic inflammation and angiogenesis are codependent, with the proliferation, migration and recruitment of tissue and inflammatory cells capable, through direct and indirect means, of stimulating angiogenesis. Likewise, angiogenesis contributes to inflammatory pathology through the creation of new blood vessels that sustain the chronic inflammatory state by transporting inflammatory cells and supplying nutrients and oxygen to the inflamed tissue (Jackson et al., *FASEB Journal*, (1997), 11:457-65). Several angiogenic inducers have been identified as having a role in RA, including FGF2; VEGF; TGFβ; TNFα; chemokines, such as IL8, IL18, and IL1; soluble adhesion molecules, such as E-selectin and soluble VCAM-1; glycoconjugates, such as the soluble 4A11 antigen, soluble CD 146 and the angiopoietin-Tie system (Koch, *Ann. Rheum. Dis*. (2003), 62(Suppl. II):ii60-ii67).

Joints affected by RA have been shown to be hypoxic. Contributing factors to hypoxia in RA joints include the high metabolic demand of inflamed synovial tissue and the rapid rate of synovial proliferation which quickly outgrows the supporting vasculature (Taylor et al., *Current Opinion in Rheumatology* (2005), 17:293-98). Tissue hypoxia in a rheumatoid joint results in increased VEGF mRNA stability and enhanced VEFG gene expression through the binding of hypoxia inducible factor-1 (HIF-1) (Richard et al., *Biochem Biophys Res Commun*. (1999), 266:718-22). HIF-1, which is made up of HIF-1α and hydroxycarbon nuclear translocator (ARNT), controls many transcription responses to hypoxia by binding the hypoxia response elements in target genes like the VEGF gene (Jones et al., *Cancer J Sci Am.* (1998), 4:209-17). HIF-1 is overexpressed in the synovial lining and stromal cells of RA patients relative to synovial tissues from individuals without RA (Hollander et al., *Arthritis Rheum.* (2001), 44:1540-44 and Giatromanolaki et al., *Arthritis Res Ther.* (2003), 5:R193-R201). VEGF is also intimately linked with the processes of immune regulation as a number of cytokines and growth factors regulate its expression in different cell types including interleukin 1β, TGFβ, FGF-2, and TNFα. Studies have shown a synergestic interaction between growth factors and hypoxia in VEGF induction (Brenchley, *Ann Rheu Dis* (2001), 60:iii71-iii74).

Several compounds have been used to inhibit angiogenesis. One such compound is 2-methoxyestradiol (2ME2). 2ME2 is a naturally occurring derivative of estradiol and has been shown to be an orally active, well-tolerated, small molecule that possess anti-proliferative and anti-angiogenic activity (Pribluda et al., *Cancer Metastasis Rev.* (2000), 19(1-2):173-9). 2ME2 has low affinity for estrogen receptors, α and β, and its anti-proliferative activity is independent of the interaction with those receptors (LaVallee et al. *Cancer Research* (2002), 62(13):3691-7). Several mechanisms have been proposed for 2ME2 activity, including those mediated by its ability to bind to the colchicines binding site of tubulin (Cushman et al., 1995; D'Amato et al., 1994), destabilization of microtubules and inhibition of HIF-1α nuclear accumulation (Mabjeesh et al., *Cancer Cell*, (2003) 3:363-75), induction of the extrinsic apoptotic pathway through upregulation of Death Receptor 5 (LaVallee et al., *Cancer Research* (2003), 63(2):469-75) and induction of the intrinsic apoptotic pathway, potentially through the inhibition of superoxide dismutase enzymatic activity (Huang et al., *Trends Cell Biology* (2001), 11(8):343-8).

What is needed are methods and compositions capable of stopping progression and/or reversing the progression of both early and late stage rheumatic diseases without unwanted or undesirable complications or side effects.

SUMMARY OF THE INVENTION

The present invention comprises methods and compositions for treating rheumatic diseases. In a disclosed embodiment, the composition comprises 2-methoxyestradiol, and derivatives thereof, in combination with anti-rheumatic agents. 2-Methoxyestradiol is a powerful antiangiogenic agent and has the ability to enhance the effects of other anti-rheumatic agents through its own anti-angiogenic and anti-proliferative capabilities.

Another disclosed embodiment comprises a method of treating rheumatic diseases comprising administering to a human or an animal an amount of a compound having the formula

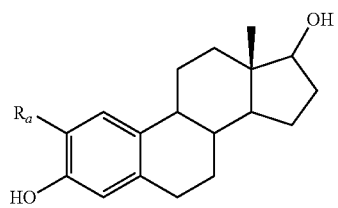

wherein $R_a$ is selected from —OCH$_3$, —OCH$_2$CH$_3$, —CH$_3$, —CH$_2$CH$_3$, —CCCH$_3$, —CHCH—CH$_3$, or CH$_2$—CHCH$_2$; and one or more anti-rheumatic agents.

Another embodiment comprises a composition for treating rheumatic diseases. The composition comprise a compound having the formula

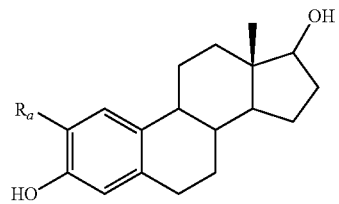

wherein $R_a$ is selected from —OCH$_3$, —OCH$_2$CH$_3$, —CH$_3$, —CH$_2$CH$_3$, —CCCH$_3$, —CHCH—CH$_3$, or CH$_2$—CHCH$_2$; and one or more anti-rheumatic agents.

Accordingly, it is an object of the present invention to provide an improved method and composition for treating rheumatic diseases in humans and animals.

Another object of the present invention is to provide an improved method and composition for treating rheumatoid arthritis in humans and animals.

A further object of the present invention is to provide a method and composition for treating rheumatic diseases in humans or animals which has few or no unwanted or undesirable side effects.

These and other objects, features and advantages of the present invention will become apparent after a review of the following detailed description of disclosed embodiments and the appended drawing and claims.

BRIEF DESCRIPTION OF THE DRAWINGS

FIG. 6 is a table which show the assessment of histomorphometric alterations following 2ME2 treatment in the Arthrogen-CIA® model of RA.

DETAILED DESCRIPTION OF THE INVENTION

Figure 1:
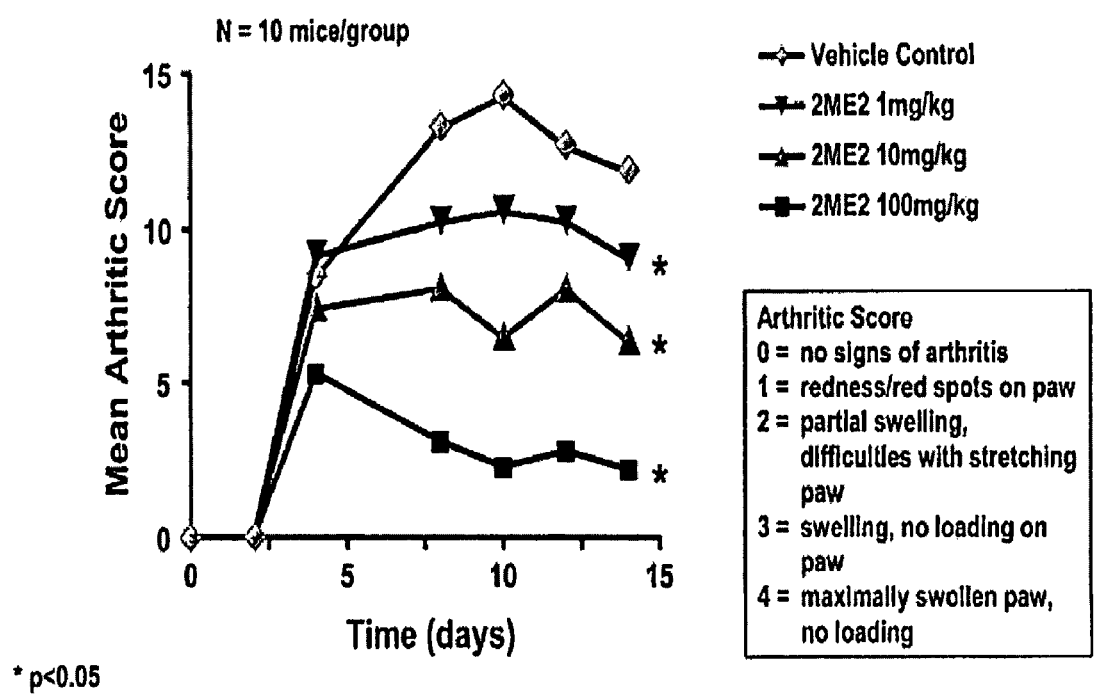
FIG. 1 is a graph which shows that administration of 2ME2 decreases the arthritic score in the Arthrogen-CIA® model of RA
Figure 2:
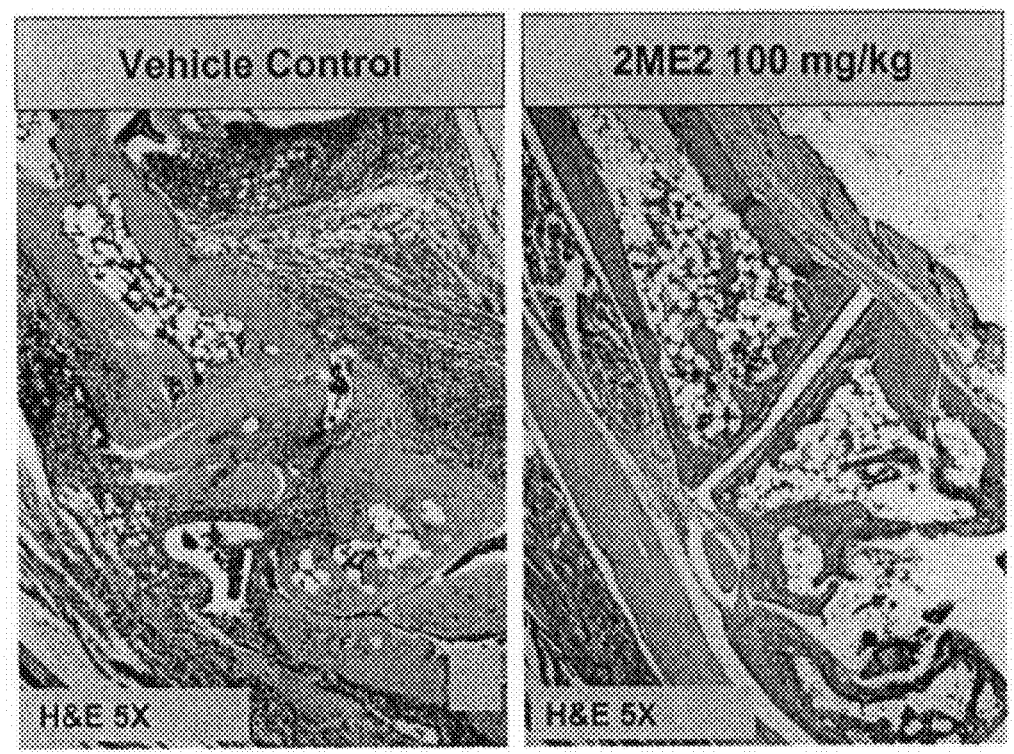
FIG. 2 is two photographs of a control and 100 mg/kg treatment which show administration of 2ME2 inhibits synovial inflammation in the Arthrogen-CIA® model of RA
Figure 3:
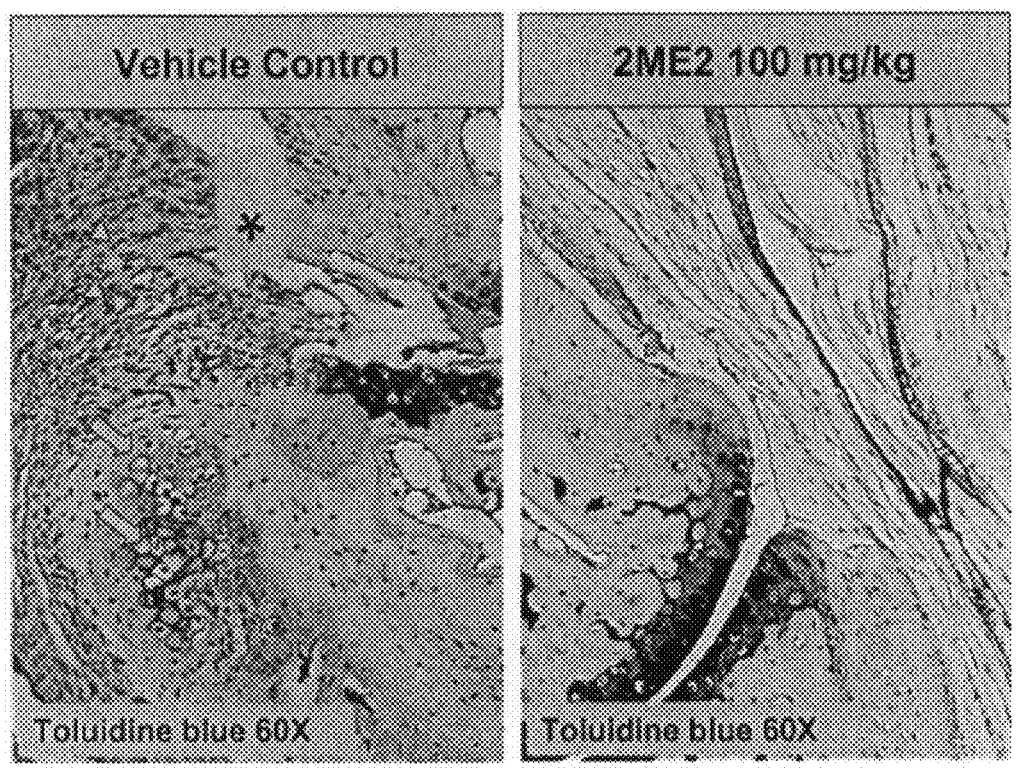
FIG. 3 is two photographs of a control and 100 mg/kg treatment which show the inhibition of periarticular inflammatory infiltrate and fibrosis by 2ME2 in the Arthrogen-CIA® model of RA.
Figure 4:
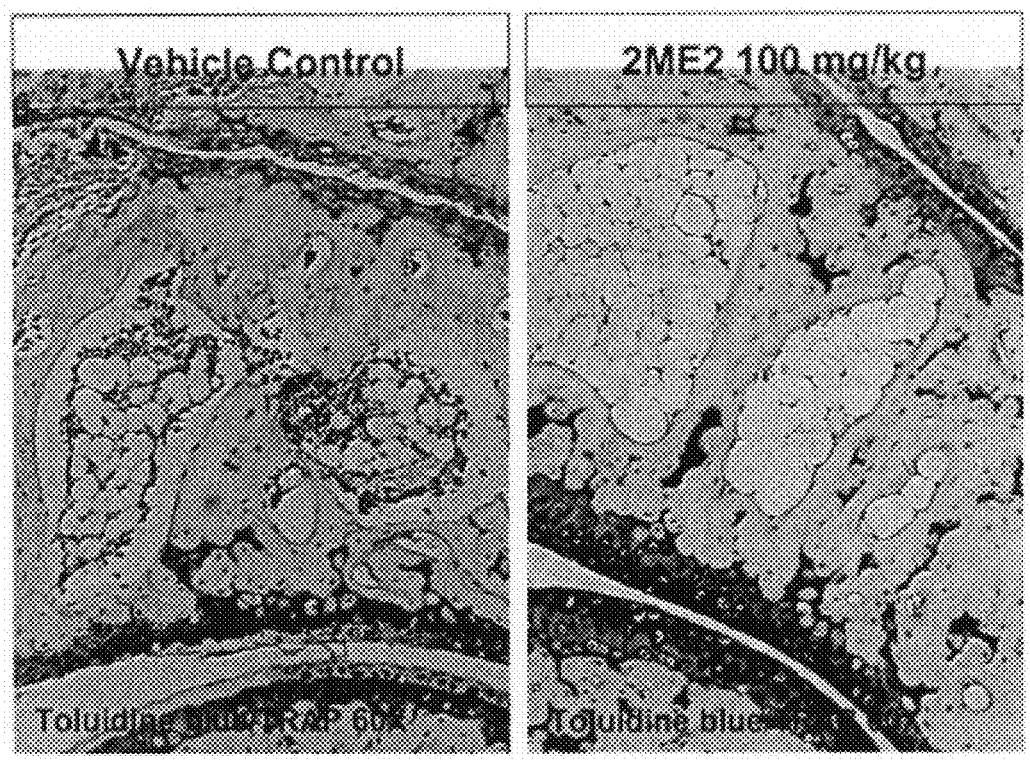
FIG. 4 is two photographs of a control and 100 mg/kg treatment which show that 2ME2 prevents loss of proteoglycan in articular cartilage and induction of osteoclast activity.
Figure 5:
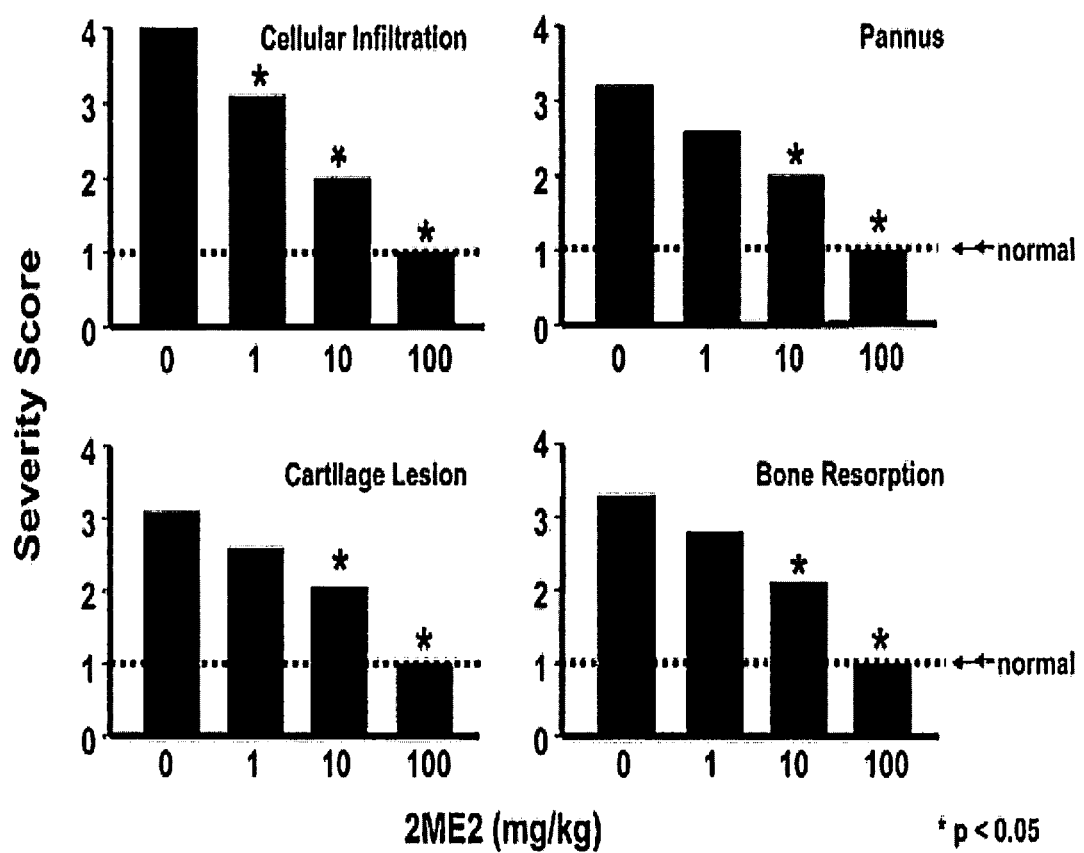
FIG. 5 is a series of graphs which show that administration of 2ME2 can inhibit the severity of RA progression in the Arthrogen-CIA® model of RA.
Figure 7:
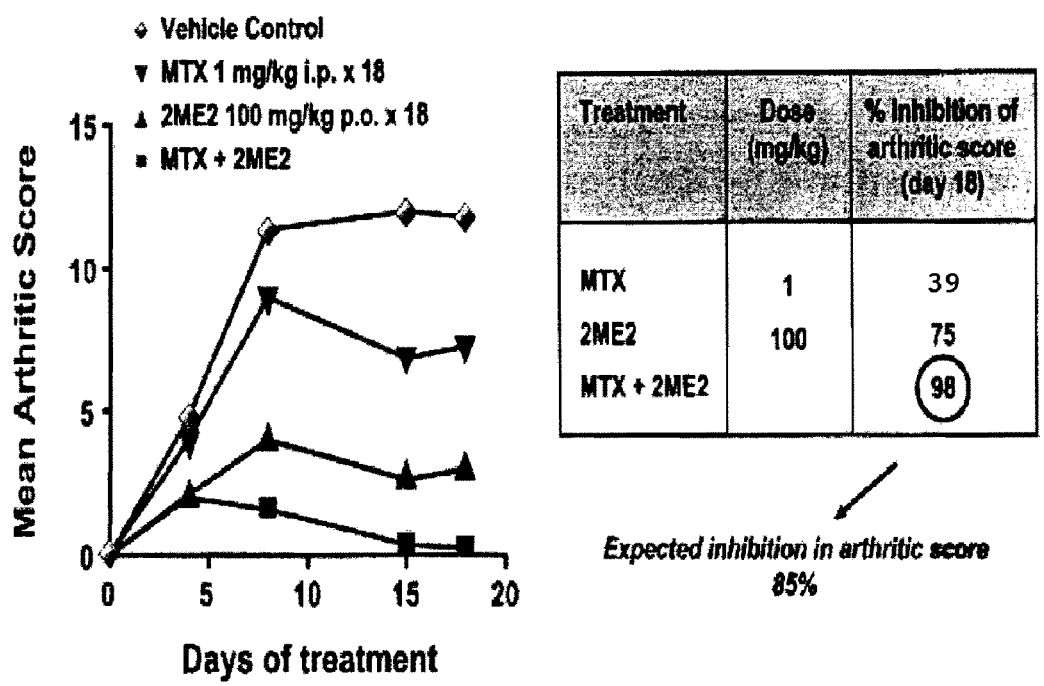
FIG. 7 is a graph and a table which show that administration of 2ME2 in combination with methotrexate results in an unexpected increase in percent inhibition of arthritic score of Arthrogen-CIA® model of RA.
Figure 8:
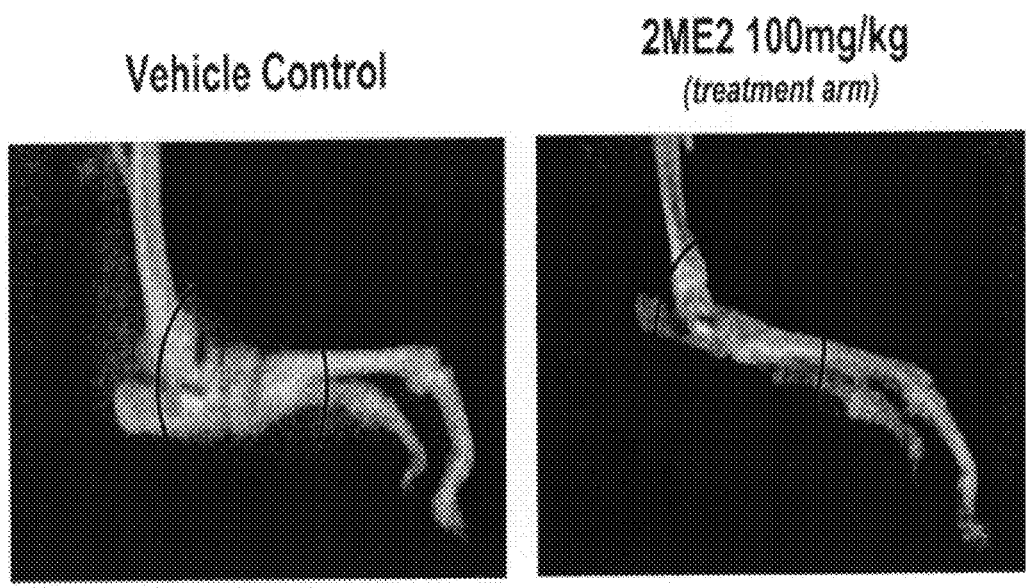
FIG. 8 is two photographs which show radiographic evidence of 2ME2's anti-rheumatic effect. in Arthrogen-CIA® model of RA.

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference.

The present invention comprises methods and compositions for treating rheumatic diseases in humans and animals. In a disclosed embodiment of the present invention, the composition comprises an anti-angiogenic and anti-proliferative agent in combination with one or more anti-rheumatic agents. The anti-angiogenic and anti-proliferative agent is 2ME2, and derivatives thereof, as shown in Formula I below.

2-Methoxyestradiol and Derivatives Thereof

The process or processes by which 2ME2 exhibits its anti-proliferative and anti-angiogenic activities remains unclear, however, a number of studies have implicated various mechanisms of action and cellular targets. 2ME2 induced changes in the levels and activities of various proteins involved in the progression of the cell cycle. These include cofactors of DNA replication and repair, e.g., proliferating cell nuclear antigen (PCNA) (Klauber, N., Parangi, S., Flynn, E., Hamel, E. and D'Amato, R. J. "Inhibition of angiogenesis and breast cancer in mice by the microtubule inhibitors 2-methoxyestradiol and Taxol," *Cancer Research*, (1997) 57:81-86; Lottering, M-L., de Kock, M., Viljoen, T. C., Grobler, C. J. S. and Seegers, J. C. "17β-Estradiol metabolites affect some regulators of the MCF-7 cell cycle," *Cancer Letters*, (1996) 110:181-186); cell division cycle kinases and regulators, e.g., p34$^{cdc2}$ and cyclin B (Attalla, H., Mäkelä, T. P., Adlercreutz, H. and Andersson, L. C. "2-Methoxyestradiol arrests cells in mitosis without depolymerizing tubulin," *Biochemical and Biophysical Research Communications*, (1996) 228:467-473; Zoubine, M. N., Weston, A. P., Johnson, D. C., Campbell, D. R. and Banerjee, S. K. "2-Methoxyestradiol-induced growth suppression and lethality in estrogen-responsive MCF-7 cells may be mediated by down regulation of p34cdc2 and cyclin B1 expression," *Int J Oncol.*, (1999) 15:639-646); transcription factor modulators, e.g., SAPK/JNK (Yue, T-L., Wang, X., Louden, C. S., Gupta, L. S., Pillarisetti, K., Gu, J-L., Hart, T. K., Lysko, P. G. and Feuerstein, G. Z. "2-Methoxyestradiol, an endogenous estrogen metabolite induces apoptosis in endothelial cells and inhibits angiogenesis: Possible role for stress-activated protein kinase signaling pathway and fas expression," *Molecular Pharmacology*, (1997) 51:951-962; Attalla, H., Westberg, J. A., Andersson, L. C., Aldercreutz, H. and Makela, T. P. "2-Methoxyestradiol-induced phosphorylation of bcl-2: uncoupling from JNK/SAPK activation," *Biochem and Biophys Res Commun.*, (1998) 247:616-619); and regulators of cell arrest and apoptosis, e.g., tubulin (D'Amato, R. J., Lin, C. M., Flynn, E., Folkman, J. and Hamel, E. "2-Methoxyestradiol, and endogenous mammalian metabolite, inhibits tubulin polymerization by interacting at the colchicine site.," *Proc. Natl. Acad. Sci. USA*, (1994) 91:3964-3968; Hamel, E., Lin, C. M., Flynn, E. and D'Amato, R. J. "Interactions of 2-methoxyestradiol, and endogenous mammalian metabolite, with unpolymerized tubulin and with tubulin polymers," *Biochemistry*, (1996) 35:1304-1310), p21$^{WAF1/CIP1}$ (Mukhopadhyay, T. and Roth, J. A. "Induction of apoptosis in human lung cancer cells after wild-type p53 activation by methoxyestradiol," *Oncogene*, (1997) 14:379-384), bcl-2 and FAS (Yue et al. (1997); Attalla et al. (1998)), and p53 (Kataoka, M., Schumacher, G., Cristiano, R. J., Atkinson, E. N., Roth, J. A. and Mukhopadhyay, T. "An agent that increases tumor suppressor transgene product coupled with systemic transgene delivery inhibits growth of metastatic lung cancer in vivo," *Cancer Res.*, (1998) 58:4761-4765; Mukhopadhyay et al. (1997); Seegers, J. C., Lottering, M-L., Grobler C. J. S., van Papendorp, D. H., Habbersett, R. C., Shou, Y. and Lehnert B. E. "The mammalian metabolite, 2-methoxyestradiol, affects p53 levels and apoptosis induction in transformed cells but not in normal cells," *J. Steroid Biochem. Molec. Biol.*, (1997) 62:253-267). The effects on the level of cAMP, calmodulin activity and protein phosphorylation may also be related to each other. More recently, 2ME2 was shown to upregulate Death Receptor 5 and caspase 8 in human endothelial and tumor cell lines (LaVallee T M, Zhan X H, Johnson M S, Herbstritt C J, Swartz G, Williams M S, Hembrough W A, Green S J, Pribluda V. S. "2-Methoxyestradiol up-regulates death receptor 5 and induces apoptosis through activation of the extrinsic pathway," *Cancer Res*. (2003) 63(2):468-75), destabilize microtubules and inhibit HIF-1α nuclear accumulation (Mabjeesh et al., *Cancer Cell*, (2003) 3:363-75), and interact with superoxide dismutase (SOD) 1 and SOD 2 and to inhibit their enzymatic activities (Huang, P., Feng, L., Oldham, E. A., Keating, M. J., and Plunkett, W. "Superoxide dismutase as a target for the selective killing of cancer cells," *Nature*, (2000) 407:390-5). All cellular targets described above are not necessarily mutually exclusive to the inhibitory effects of 2ME2 in actively dividing cells.

The more relevant mechanisms described above have been extensively discussed in Victor S. Pribluda, Theresa M. LaVallee and Shawn J. Green, 2-*Methoxyestradiol*: A *novel endogenous chemotherapeutic and antiangiogenic* in The New Angiotherapy, Tai-Ping Fan and Robert Auerbach eds., Human Press Publisher.

The anti-angiogenic and anti-proliferative portion of the composition according to the disclosed embodiment of the present invention comprises a compound of Formula I:

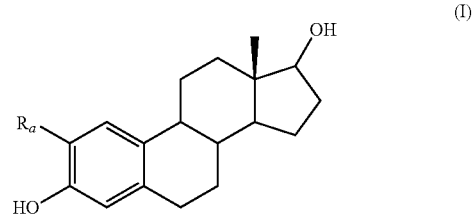

(I)

wherein $R_a$ is selected from —OCH$_3$, —OCH$_2$CH$_3$, —CH$_3$, —CH$_2$CH$_3$, —CCCH$_3$, —CHCH—CH$_3$, or CH$_2$—CHCH$_2$. In cases where stereoisomers are possible, both R and S stereoisomers are envisioned, as well as any mixture of stereoisomers.

Those skilled in the art will appreciate that the invention extends to other 2-methoxyestradiol analogs within the definitions given and in the claims below, having the described characteristics. These characteristics can be determined for each test compound using assays known in the art.

Anti-Rheumatic Agents

Anti-rheumatic agents that may be used with the disclosed embodiment of the present invention include, but are not limited to, disease-modifying anti-rheumatic drugs, non-steroid anti-inflammatory drugs, corticosteroids, tumor necrosis factor inhibitors, selective B-cell inhibitors, interleukin-1 inhibitors and mixtures or combinations thereof. Each of these anti-rheumatic agents is discussed further below.

Disease-Modifying Anti-Rheumatic Drugs

Disease-modifying anti-rheumatic drugs that may be used with the disclosed embodiment of the present invention include, but are not limited to, allopurinol, amitriptyline hydrochloride, auranofin (oral gold), azathiopine, chlorambucil, colchicine, cyclobenzaprine cyclophosphamide, cyclosporine, dulozetine, fluoxetine, gold sodium thiomalate (injectable gold), hydroxychloroquine sulfate, leflunomide, methotrexate, minocycline, mycophenolate mofetil, probenecid, sulfasalazine, tamadol and mixtures or combinations thereof.

Non-Steroid Anti-Inflammatory Drugs

Non-steroid anti-inflammatory drugs that may be used with the disclosed embodiment of the present invention include, but are not limited to, traditional NSAIDS, such as diclofenac potassium, diclofenac sodium, diclofenac sodium with misoprostol, diflunisal, etodolac, fenoprofen calcium, flurbiprofen, ibuprofen, indomethacin, ketoprofen, meclfenamate sodium, mefenamic acid, meloxicam, nabumetone, naproxen, oxaprozin, piroxicam, sulindac, and tolmetin sodium; COX-2 inhibitors, such as celecoxib, rofecoxib, and valdecoxib; salicylates, such as aspirin, choline salicylate, salsalate, and sodium salicylate; bisphonates, such as alendronate, ibandronate, and risedronate.

Corticosteroids

Corticosteroids that may be used with the disclosed embodiment of the present invention include, but are not limited to, betamethasone, cortisone acetate, dexamethasone, hydrocortisone, methylprednisolone, prednisolone, prednisone and mixtures or combinations thereof.

Tumor Necrosis Factor Inhibitors

Tumor necrosis factor inhibitors that may be used with the disclosed embodiment of the present invention include, but are not limited to, adalimumab, etanercept, infliximab, abatacept and mixtures or combinations thereof.

Selective B-cell Inhibitors

Selective B-cell inhibitors that may be used with the disclosed embodiment of the present invention include, but are not limited to, rituximab.

Interleukin-1 Inhibitors

Interleukin-1 inhibitors that may be used with the disclosed embodiment of the present invention include, but are not limited to, anakinra.

Administration

In accordance with the present invention, the compounds of Formula I may be mixed with one or more anti-rheumatic agents into a single formulation. The compounds of Formula I and the anti-rheumatic agent may also be formulated and delivered separately.

The compositions described herein can be provided as physiologically acceptable formulations using known techniques, and the formulations can be administered by standard routes. In general, compounds of Formula I and the anti-rheumatic agent can be administered by topical, oral, rectal or parenteral (e.g., intravenous, subcutaneous or intramuscular) route. In addition, the compositions can be incorporated into polymers allowing for sustained release, the polymers being implanted in the vicinity of where delivery is desired, for example, at the site of inflammation or within or near an affected joint, or the polymers can be implanted, for example, subcutaneously or intramuscularly or delivered intravenously or intraperitoneally to result in systemic delivery of compounds of Formula I and/or anti-rheumatic agent. Other formulations for controlled, prolonged release of therapeutic agents useful in the present invention are disclosed in U.S. Pat. No. 6,706,289, the disclosure of which is incorporated herein by reference.

The formulations in accordance with the present invention can be administered in the form of a tablet, a capsule, a lozenge, a cachet, a solution, a suspension, an emulsion, a powder, an aerosol, a suppository, a spray, a pastille, an ointment, a cream, a paste, a foam, a gel, a tampon, a pessary, a granule, a bolus, a mouthwash, or a transdermal patch.

The formulations include those suitable for oral, rectal, nasal, inhalation, topical (including dermal, transdermal, buccal and sublingual), vaginal, parenteral (including subcutaneous, intramuscular, intravenous, intradermal, intraocular, intratracheal, and epidural) or inhalation administration. The formulations can conveniently be presented in unit dosage form and can be prepared by conventional pharmaceutical techniques. Such techniques include the step of bringing into association the active ingredient and a pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored base, usually sucrose and acacia or tragacanth; pastilles comprising the active ingredient in an inert base such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. In one embodiment the topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken; i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Formulations suitable for parenteral administration also include, but are not limited to, nanoparticle formulations made by numerous methods as disclosed in U.S. patent application Ser. No. 10/392,403 (Publication No. US 2004/0033267), U.S. patent application Ser. No. 10/412,669 (Publication No. US 2003/0219490), U.S. Pat. No. 5,494,683, U.S. patent application Ser. No. 10/878,623 (Publication No. US 2005/0008707), U.S. Pat. Nos. 5,510,118, 5,524,270, 5,145,684, 5,399,363, 5,518,187, 5,862,999, 5,718,388, and 6,267,989, all of which are hereby incorporated herein by reference in there entirety. A review of drug formulation technology is provided in "Water Insoluble Drug Formulation" by Rong Liu, editor, pp. 1-633, (2000) CRC Press LLC, which is incorporated herein by reference in its entirety.

By forming 2-methoxyestradiol nanoparticles, the compositions disclosed herein are shown to have increased bioavailability. Preferably, the particles are comprised of the compounds of Formula I and/or anti-rheumatic agents alone or in combination, with accessory ingredients or in a polymer for sustained release. The particles of the compounds of the present invention have an effective average particle size of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 run, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods well known to those of ordinary skill in the art. It is understood that the particle sizes are average particle sizes and the actual particle sizes will vary in any particular formulation. Often, surface stabilizers are used to form stable nanoparticles; however, this method of forming nanoparticles is only one of many different methods of forming effective nanoparticle compositions. The formulations may be presented in unit-dose or multi-dose containers, for example, sealed ampules and vials, and may be stored in freeze-dried (lyophilized) conditions requiring only the addition of a sterile liquid carrier, for example, water for injections, immediately prior to use. Extemporaneous injection solutions and suspensions may be prepared from sterile powders, granules and tablets of the kinds previously described.

In one embodiment, the compounds of Formula I and the anti-rheumatic agent can be administered simultaneously. In another embodiment, they can be administered separately (i.e.; compounds of Formula I dosage in the morning, anti-rheumatic agent dosage in the evening). Mixtures of more than one anti-rheumatic agent can, of course, be administered. Indeed, it is often desirable to use mixtures or sequential administrations of different anti-rheumatic agents to treat rheumatic disease, especially anti-rheumatic agents from the different classes.

If the 2-methoxyestradiol formulation and the anti-rheumatic agent are to be administered sequentially, the amount of time between administration of the 2-methoxyestradiol formulation and the anti-rheumatic agent will depend upon factors such as the amount of time it take the 2-methoxyestradiol formulation to be fully incorporated into the circulatory system of the host and the retention time of the 2-methoxyestradiol formulation in the host's body. In one embodiment, dosage formulations for 2-methoxyestradiol are disclosed in U.S. patent application Ser. No. 11/288,989, filed Nov. 29, 2005, which is incorporated herein by reference in its entirety.

The anti-rheumatic agent is administered in a therapeutically effective amount. This amount will be determined on an individual basis and will be based, at least in part, on consideration of the host's size, the specific disease to be treated, the severity of the symptoms to be treated, the results sought, and other such considerations. An effective amount can be determined by one of ordinary skill in the art employing such factors and using no more than routine experimentation.

It should be understood that, in addition to the ingredients particularly mentioned above, the formulations of the present invention may include other agents conventional in the art having regard to the type of formulation in question, for example, those suitable for oral administration may include flavoring agents, and nanoparticle formulations (e.g.; less than 2000 nanometers, preferably less than 1000 nanometers, most preferably less than 500 nanometers in average cross section) may include one or more than one excipient chosen to prevent particle agglomeration.

Pharmaceutical Preparations

Also contemplated by the present invention are implants or other devices comprised of the formulation in accordance with the disclosed embodiments, or prodrugs thereof, or other compounds included by reference where the drug or prodrug is formulated in a biodegradable or non-biodegradable polymer for sustained release. Non-biodegradable polymers release the drug in a controlled fashion through physical or mechanical processes without the polymer itself being degraded. Biodegradable polymers are designed to gradually be hydrolyzed or solubilized by natural processes in the body, allowing gradual release of the admixed drug or prodrug. The drug or prodrug can be chemically linked to the polymer or can be incorporated into the polymer by admixture. Both biodegradable and non-biodegradable polymers and the process by which drugs are incorporated into the polymers for controlled release are well known to those skilled in the art. Examples of such polymers can be found in many references, such as Brem et al., *J. Neurosurg* 74: pp. 441-446 (1991). These implants or devices can be implanted in the vicinity where delivery is desired, for example, at the site of a tumor or a stenosis, or can be introduced so as to result in systemic delivery of the agent.

Because anything not formed in the body as a natural component may elicit extreme and unexpected responses, such as blood vessel closure due to thrombus formation or spasm, and because damage to blood vessels by the act of insertion of a vascular stent may be extreme and unduly injurious to the blood vessel surface, it is prudent to protect against such events. Restenosis is a re-narrowing or blockage of an artery at the same site where treatment, such as an angioplasty or stent procedure, has already taken place. If restenosis occurs within a stent that has been placed in an artery, it is technically called "in-stent restenosis," the end result being a narrowing in the artery caused by a build-up of substances that may eventually block the flow of blood. The compounds that are part of the present invention are especially useful to coat vascular stents to prevent restenosis. The coating should preferably be a biodegradable or non-biodegradable polymer that allows for a slow release of a compound of the present invention thereby preventing the restenosis event.

The present invention also relates to conjugated prodrugs and uses thereof. More particularly, the invention relates to conjugates of steroid compounds, such as compounds of Formula I, and the use of such conjugates in the prophylaxis or treatment of conditions associated with rheumatic or related inflammatory diseases. The invention also relates to compositions including the prodrugs of the present invention.

In one aspect, the present invention provides a conjugated prodrug of an estradiol compound, preferably compounds of Formula I, conjugated to a biological activity modifying agent.

Alternatively, the conjugated prodrug according to the present invention includes the compounds of Formula I, conjugated to a peptide moiety.

The incorporation of an estradiol compound, such as the compounds of Formula I, into a disease-dependently activated pro-drug enables significant improvement of potency and selectivity of this anti-angiogenic agent.

A person skilled in the art will be able by reference to standard texts, such as Remington's Pharmaceutical Sciences 17th edition, to determine how the formulations are to be made and how these may be administered.

In a further aspect of the present invention there is provided use of compounds of Formula I, or prodrugs thereof, in combination with an anti-rheumatic agent according to the present invention for the preparation of a medicament for the prophylaxis or treatment of rheumatic diseases.

In a still further aspect of the present invention there is provided a method of prophylaxis or treatment of a rheumatic disease, said method including administering to a patient in need of such prophylaxis or treatment an effective amount of compounds of Formula I, or prodrugs thereof, in combination with an anti-rheumatic agent according to the disclosed embodiment, as described herein. It should be understood that prophylaxis or treatment of said condition includes amelioration of said condition.

Pharmaceutically acceptable salts of the compounds of the Formula I, or the prodrugs thereof, can be prepared in any conventional manner, for example from the free base and acid. In vivo hydrolysable esters, amides and carbamates and other acceptable prodrugs of Formula I can be prepared in any conventional manner.

100% pure isomers are contemplated by this invention; however a stereochemical isomer (labeled as α or β, or as R or S) may be a mixture of both in any ratio, where it is chemically possible by one skilled in the art. Also contemplated by this invention are both classical and non-classical bioisosteric atom and substituent replacements, such as are described by Patani and Lavoie ("Bio-isosterism: a rational approach in drug design" Chem. Rev. (1996) p. 3147-3176) and are well known to one skilled in the art. Such bioisosteric replacements include, for example, but are not limited to, substitution of =S or =NH for =O.

A particularly useful formulation in the present invention is a nanoparticulate liquid suspension of 2-methoxyestradiol disclosed in U.S. patent application Ser. No. 10/392,403, filed Mar. 20, 2003 (the disclosure of which is incorporated herein by reference). This formulation is available from EntreMed, Inc., Rockville, Md., under the designation Panzem® NCD.

Known compounds that are used in accordance with the invention and precursors to novel compounds according to the invention can be purchased, e.g., from Sigma Chemical Co., Steraloids or Research Plus. Other compounds according to the invention can be synthesized according to known methods from publicly available precursors.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof Which, after reading the description herein, may suggest themselves to those skilled in the art without departing from the spirit of the present invention.

EXAMPLES

The data present in the Examples and the following table indicates that 2ME2 can be used in combination with a wide range of anti-rheumatic agents. The characteristics of 2ME2 and compounds of Formula I are such that they can be combined with anti-rheumatic agents at the maximally tolerated or maximally effective dose and schedule of the anti-rheumatic agent. In some embodiments, combination with 2ME2 can be used to maintain the effectiveness while reducing the dose of the anti-rheumatic agent. Such reduction in dose can result in reduction of toxicity or reduction in any unacceptable effect or side-effect of the anti-rheumatic agent.

TABLE 1

Summary of In Vivo Anti-Arthritic Activity of 2ME2 (Panzem ® NCD) Formulation

| Study Number | Dose, Schedule, Route | Mode of Intervention | Endpoint(s) Measured | Main Findings |
|---|---|---|---|---|
| EntreMed SMP04-040 Mouse (Balb/C), Female, n = 10/group Arthrogen Collagen MAb-Induced Arthritis | 1, 10, 100 mg/kg/d; Vehicle control PO | Prevention[a] | Footpad swelling Clinical arthritic score Histopathology & histomorphometric analysis of joint Immunohistochemistry | Dose-dependent inhibition of clinical arthritic score, inflammation, cartilage degradation, bone resorption, and pannus formation Inhibition of angiogenesis |
| EntreMed SMP05-010 Mouse (Balb/C), | 10, 25, 50, 75, 100 mg/kg/d; Vehicle control PO | Prevention[a] | Clinical arthritic score Histopathology & histomorphometric analysis of joint | Dose-dependent inhibition of clinical arthritic score, |

TABLE 1-continued

Summary of In Vivo Anti-Arthritic Activity of 2ME2 (Panzem ® NCD) Formulation

| Study Number | Dose, Schedule, Route | Mode of Intervention | Endpoint(s) Measured | Main Findings |
|---|---|---|---|---|
| Female n = 10/group Arthrogen Collagen MAb-induced Arthritis | | | PK | inflammation, cartilage degradation, bone resorption, and pannus formation Steady-state $AUC_{0-24}$ for 25, 50, and 75 mg/kg were 66, 117, and 301 ng · hr/mL, respectively |
| EntreMed SMP05-009 Mouse (Balb/C), Female, n = 10/group Arthrogen Collagen MAb-induced Arthritis | 100 mg/kg/d, 100 mg/kg/week, 100 mg/kg twice a week; Vehicle control PO | Prevention[a] | Clinical arthritic score Histopathology & histomorphometric analysis of joint | Regimen-dependent inhibition of clinical arthritic score, inflammation, cartilage degradation, bone resorption, and pannus formation |
| EntreMed SMP05-046 Mouse (Balb/C), Female, n = 10/group Arthrogen Collagen MAb-Induced Arthritis | 2ME2 (10 or 100 mg/kg/d) PO MTX (0.1 or 1 mg/kg/d) IP; Vehicle control | Prevention[a] | Clinical arthritic score Liver histopathology | Additive inhibition of clinical arthritic score upon combination of the two drugs No pathology in the liver with either drug alone or in combination |
| UCLA Ernie Brahn Study #1 Rat (Louvain) Female, n = 12/group Collagen-Induced Arthritis | Prevention: 30, 100 mg/kg/d; Vehicle control PO Treatment: 10, 30, 100 mg/kg/d; Vehicle control PO | Prevention[a] & Treatment[b] | Clinical arthritic score Radiographic score | Dose dependent inhibition of clinical arthritic score and bone erosion Delays onset of disease |
| UCLA Ernie Brahn Study #2 Rat (Louvain) Female, n = 12/group Collagen-Induced Arthritis | 50 mg/kg BID, 100 or 300 mg/kg/d; Vehicle control PO OR 60 mg/kg/d SC osmotic pumps; Vehicle control SC osmotic pumps | Treatment[b] | Clinical arthritic score Radiographic score Histopathology & histomorphometric analysis of joint Immunohistochemistry | Dose dependent inhibition of clinical arthritic score, inflammation, and bone erosion, cartilage degradation and pannus formation. Inhibition of angiogenesis |
| Dalhousie University Andrew Issekutz Study #1 Rat (Lewis) Male, n = 5-9 | 30, 100 mg/kg/d; Vehicle control (1.2% HPC, 0.06% DOSS in sterile water) PO | Prevention[c] & Treatment[b] | Clinical arthritis score Histopathology of joint Histological evaluation of spleen, liver, lung, lymph nodes | Inhibition of clinical arthritic score and cartilage degradation at both doses and regimens |

TABLE 1-continued

Summary of In Vivo Anti-Arthritic Activity of 2ME2 (Panzem ® NCD) Formulation

| Study Number | Dose, Schedule, Route | Mode of Intervention | Endpoint(s) Measured | Main Findings |
|---|---|---|---|---|
| Adjuvant-Induced Arthritis | | | Immune cell migration | Decreased splenic abscess formation, giant cells, and lymphoid hyperplasia Blocked immune cell migration to the joint |
| Dalhousie University Andrew Issekutz Study #2 Rat (Lewis) Male, n = 5 Adjuvant-Induced Arthritis (Adoptive Transfer Model) | 3, 30 mg/kg/d; Vehicle control (1.2% HPC, 0.06% DOSS in sterile water) SC | Prevention[c] & Treatment[b] | Clinical arthritic score Histopathology of joint Immune cell migration Lymphocyte proliferation | Dose dependent inhibition of clinical arthritic score, inflammation, and bone destruction Inhibition of cellular infiltration to the joints Inhibition of migration of PMNs and splenocytes to dermal sites only in response to TNFα and PPD |

[a]Indicates treatment started 1 day following the induction of arthritis; clinical signs of arthritis are not evident
[b]Indicates treatment started 10 days following the induction of arthritis, clinical signs of arthritis are present
[c]Indicates treatment started 6 days following the induction of arthritis; clinical signs of arthritis are not evident The following examples provide a detailed description of the protocols used in the Dalhousie University Studies 1 and 2, in Table 1 above and are representative of the general protocols employed in assessing the disease modifying characteristics of 2ME2 alone and in combination with other anti-rheumatic agents.

Example 1

Effect of 2ME2 Treatment of Clinical Arthritis Severity

Adjuvant arthritis was induced in 6-8 week old inbred male Lewis rats (175-200 g; Charles River Canada, St-Constant, QC) by s.c. immunization with 0.5 mg of *Mycobacterium butyricum* (Gibco, Detroit, Mich.) in 0.05 mL mineral oil at two sites on each side of the base of the tail. Arthritis was scored clinically from 0-4 points per limb and tail based on severity of swelling, erythema and limitation of movement as described by Taurog et al. (Methods Enzymol. (1988), 162: 339-55).

Rats were treated with 2ME2 at two stages in the development of AA. 2ME2 was provided by EntreMed, Inc. (Rockville, Md.). Treatment was initiated either 6 days (d) following immunization, with doses of 30 mg/kg/d or 100 mg/kg/d or vehicle given i.p. in a volume of 0.5 ml, for a total of 8 d, i.e., to 14 d post-immunization. This protocol was used to start 2ME2 therapy following the initiation of the immune response but prior to the development of clinical arthritis, which normally develops by day 9 or 10. Additional groups of animals were treated with 2ME2 (100 mg/kg/d i.p.) starting on day 10 post-immunization, corresponding to the first signs of clinical arthritis (redness, usually starting in the hind paws, and limping). Treatment was continued to day 14 and all measurements were concluded by day 15 post-immunization, which was the time the animals were sacrificed.

In Lewis rats, polyarticular arthritis, typically most severe in the hind limbs, develops 9-10 days following immunization with killed *M. butyricum* (or *M. tuberculosis*) in mineral oil. The arthritis is rapidly progressive, reaching a peak clinical arthritis severity score by day 14-15 post-immunization. Rats treated with vehicle developed arthritis reaching a clinical score of 11. The vehicle-treated group developed arthritis at the same rate and maximum severity as untreated rats. Rats treated with 2ME2 at 30 mg/kg/d or 100 mg/kg/d, initiated on day 6 post-immunization, had significantly less arthritis severity by day 14 (mean=7.4 and 6.5, respectively) than the vehicle-treated group. Furthermore, rats treated with the higher dose of 2ME2 (100 mg/kg/d) initiated at the onset of clinical arthritis on day 10 post-immunization also had an attenuation of arthritis severity which was comparable to the groups in which treatment was initiated during the preclinical phase (day 6). However, the modification of arthritis severity in a group receiving the lower dose of 2ME2 (30 mg/kg/d) initiated on day 10 post-immunization did not reach statistical significance, suggesting that the higher dose was required once clinical arthritis had developed.

Example 2

Effect of 2ME2 Treatment on Neutrophil Migration to Arthritic Joints and Dermal Inflammatory Reactions Rat blood PMNL were isolated from a donor arthritic rat by hydroxyethyl starch (Hespan; Dupont Merck, Wilmington, Del.) exchange transfusion performed through a needle inserted in a femoral vein. The exchanged blood was collected into heparin and acid-citrate-dextrose (ACD, formula A; Fenwal-Travenol, Malton, ON) and the leukocyte-rich plasma was harvested during 1 g sedimentation of red blood cells. The PMNL were then isolated by centrifugation on discontinuous Percoll density gradients of 63% Percoll above 74% Percoll with 10% autologous plasma and calcium and magnesium-free Tyrode's solution ($TyS^{-/-}$) for the balance of the suspending medium. After centrifugation (350×g, 30 min at 22° C.) the purified PMNL (>95%) were harvested from the layer above the 74% plasma-Percoll cushion and after washing with $TyS^{-/-}$–10% plasma, the cells were radiolabeled with 75 μCi/5×10$^7$ cells of $Na_2{}^{51}CrO_4$ (GE Healthcare Bio-Sciences Inc., Baie d'Urfé, QC). After the cells were washed, they were injected i.v. into rats at a dose of $10^7$ $^{51}$Cr-labeled PMNL per animal bearing approximately 1-2×10$^5$ cpm. These cells were allowed to circulate and migrate for 2 h prior to sacrifice of the rats.

PMNL accumulation in skin sites in the arthritic rats was measured by inducing local inflammation by intradermal (i.d.) injection (0.05 ml) of rat TNF-α (Peprotech, Rocky Hill, N.J.), E. coli endotoxin (LPS; List Biologicals, Campbell, Calif.) or zymosan-activated serum (rat) as a source of $C5a_{desArg}$.[22] 2 h before sacrifice, administered in the doses indicated at the same time as the i.v. injection of radiolabeled PMNL. The accumulation of PMNL in these sites was quantified by biopsy of the injection sites using a 12-mm punch biopsy taken following sacrifice of the animals.

At the time the rats were killed, cardiac blood was obtained to measure the blood leukocyte count and the leukocyte and plasma associated radioactivity. Joints were dissected and segments of limbs sectioned to include carpal, metacarpal, talar and metatarsal joints for analysis as previously reported (Issekutz et al. Lab Invest. (1991), 64:656-63 and Issekutz et al. Arthritis Rheum. (2001), 44:1428-37). The content of $^{51}$Cr in the joints, as well as in dermal skin sites and internal organs, was determined with a Wallac LKB 1280 gamma counter (Fisher Scientific, Nepean, ON). Accumulated isotope in the tissue was expressed as cpm/$10^6$ cpm injected i.v.

We have previously shown that radiolabeled blood PMNL migration to the joints of rats with AA develops rapidly during the second week post-immunization and peaks by day 14-15, this being most intense in the hind limb joints, i.e., the talar and metatarsal joints, with lesser accumulation in the forelimb carpal and metacarpal joints (Issekutz et al. (1991) 2ME2 treatment initiated during the preclinical phase at day 6, at either 100 or 30 mg/kg/d, significantly decreased the accumulation of $^{51}$Cr-labeled PMNL in the most intensely involved joints of the hind limbs, and to a lesser degree and somewhat more variably in the forelimb joints. However, although there was a tendency for a decrease in the group receiving delayed 2ME2 treatment starting on day 10, when arthritis had clinically developed, this did not reach significance.

In the same rats, the migration of PMNL to dermal inflammatory reactions was measured, these reactions being initiated at the time of radiolabeled PMNL injection. Thus the migration quantitated the acute reaction during the first two hours of the lesions. 2ME2 treatment did not affect PMNL migration to the complement chemotactic factor $C5a_{des-arg}$ or to E. coli LPS. In contrast, the PMNL migration to sites injected with rat TNF-α was inhibited by approximately 50% in rats that were treated with 2ME2 at either dose tested, starting at day 6 post-immunization. There was a tendency for inhibition by 2ME2 in the group in which treatment was delayed to day 10, but this did not reach significance. It should be noted that rats with AA develop a leukocytosis with marked neutrophilia (Taurog (1988) and Issekutz (1991) This response was not affected by 2ME2 treatment initiated either on day 6 or day 10 at either dose tested. Thus the observed effects could not be attributed to differences in blood PMNL counts. Furthermore, there was no difference between any of the groups in the level of radiolabeled $^{51}$Cr PMNL in the circulation during the 2-h migration period.

Example 3

Effect of 2ME2 Treatment on Joint Histology and Cartilage Damage

Tissue samples, including joints, were fixed in 10% phosphate-buffered formalin or AFA fixative (75% ethyl alcohol, 2% formalin, 5% glacial acetic acid, 20% water), the latter for immunostaining. Samples were then decalcified in formic or acetic acid and paraffin embedded. Sections (5 μm) were stained with hematoxylin-eosin (H&E) using routine techniques. To stain cartilage proteoglycan, separate sections were stained with safranin O (Difco, Detroit, Mich.) for 1 min. as described previously (Issekutz, (2001). To assess microvessel density in the synovium, rabbit anti-mouse laminin polyclonal IgG antibody (Cedarlane Laboratories Limited, Homby, ON) was used to outline vessels, with detection using biotinylated goat anti-rabbit IgG antibody and avidin-biotin complexed with HRPO according to manufacturer's recommendations (Vectastain Elite ABC kit; Vector Laboratories Canada Inc., Burlington, ON).

Joints from a vehicle-treated rat showed that the synovium is markedly thickened and intensely infiltrated by leukocytes with marked synovial expansion. Even by the H&E staining the cartilage damage is visible on the articular surfaces and margins. This is more profoundly illustrated by the safranin O staining with marked focal proteoglycan loss and fragmentation. 2ME2-treated rats that received 100 mg/kg/d initiated at day 6 post-immunization, showed less intense leukocyte infiltration of the synovium when compared to vehicle treated, although clearly synovial infiltration and expansion have occurred. However, most notable is the preservation of articular cartilage surfaces and proteoglycan staining. Similar changes were observed in rats treated with 30 mg/kg/d from day 6, but in rats in which 2ME2 treatment was delayed to day 10, the leukocyte cellularity in the synovium was less noticeably affected. Nevertheless, cartilage preservation was still observed.

Example 4

Effect of 2ME2 Treatment on Synovial Vascularity

To assess synovial vascularity and angiogenesis, sections were immunostained for laminin to reliably delineate microvessels as well as medium-sized vessels. This technique was found to be more reliable than staining for von Willebrand factor (factor VIII related antigen), since it was observed that staining for von Willebrand factor was diminished or absent in areas where there was intense leukocyte infiltration, even though microvessels were obviously present. The other commonly used endothelial cell marker, CD31, was also evaluated on the synovial tissue. Although a monoclonal antibody to rat CD31 clearly stained vascular endothelium, CD31 was also present on infiltrating leukocytes, which complicated the interpretation. The antibody to mouse laminin used here specifically stained vessels of capillary size and larger, presumably reacting with the basement membrane laminin. The immunohistochemistry of synovium from a vehicle-treated rat, revealing the intense vascularity of the leukocyte-infiltrated synovium. The vascularity in the synovium of a rat treated with 100 mg/kg/d of 2ME2 starting on day 6 post-immunization showed less intense leukocyte infiltrate in the synovium, but synovial vascularity is still prominent. This vascularity was quantitated in synovia from rats treated with the various protocols and compared to vehicle-treated animals. The synovia were examined for small (1-2 RBC diameters), medium (3-5 RBC diameters) and large (diameter greater than 5 RBC diameters or >30 μm) vessels. Only vessels that were in cross-section were scored. There was no significant difference in the vessel density per 0.8 mm$^2$ between the various treatment groups at any of the vessel sizes. This confirmed the impression from the immunohistochemical staining that, although leukocyte infiltration was attenuated by 2ME2 treatment, neovascularization was not appreciably modified.

Example 5

Effect of 2ME2 Treatment on Endothelial Cell Proliferation under Minimal and Optimal Growth Conditions Because of the lack of a clear effect of 2ME2 therapy on synovial angiogenesis, the effect of 2ME2 on endothelial cell proliferation in vitro under optimal endothelial cell growth stimulatory conditions, likely to be present in vivo in the synovium during arthritis, was examined. The endothelial inhibitory effect of 2ME2 has generally been evaluated under conditions of restricted serum and growth factor as a means of optimally observing the effect of 2ME2 on endothelial growth. The inhibition of endothelial cell proliferation by 2ME2 is dose-dependent under conditions of restricted serum and growth factor with significant inhibition at 0.25 μg/mL of 2ME2. Under conditions of optimal serum and endothelial cell growth supplements, 2ME2 was still capable of inhibiting endothelial cell proliferation in a dose-dependent fashion, although this required approximately a two-fold higher concentration of 2ME2. Under these optimal growth conditions, the IC$_{50}$ was approximately 0.5 μg/mL (approximately 1.5× 10$^{-6}$ M). These findings demonstrate that 2ME2 inhibited endothelial cell proliferation even under optimal growth conditions, despite the fact that it seemed to have little observed effect on angiogenesis in the arthritic synovium during in vivo treatment.

Example 6

Effect of 2ME2 Treatment on Splenomegaly

During the course of AA in the rat, splenomegaly is a prominent feature due to splenitis, lymphoid hyperplasia and even abscess formation. Therefore the splenic enlargement in these animals was monitored for any effect of 2ME2 on this parameter. In rats that were treated with vehicle, spleen weights increased dramatically, increasing nearly three-fold. This was completely inhibited by 2ME2 treatment started on day 6 post-immunization by the high dose, but also by the more moderate dose of 30 mg/kg/d. Furthermore, even when 2ME2 treatment was initiated during the late stage of AA development, i.e., at day 10, the splenic enlargement was still markedly inhibited.

A histological examination of the spleens was undertaken in the different groups. The appearance of a normal rat spleen (A) and vehicle-treated spleen (B). The latter shows the severe splenitis involving the red pulp and even the capsule. Furthermore, the spleen demonstrated extensive PMNL and mononuclear cell accumulation with abscess formation and some cellular necrosis. There were also increased numbers of multinucleated giant cells and lymphoid hyperplasia in the white pulp. Only mild splenitis was visible in a rat treated with 2ME2 (30 mg/kg/d) from day 6-14 post-immunization, with no increase in giant cells or abscess formation, and there was no lymphoid hyperplasia observed.

Example 7

Effect of 2ME2 Treatment on Lymphocyte Response to Mitogens and Antigen

Because of the effect of 2ME2 treatment on arthritis severity and the response in the spleen during AA, the T lymphocyte reactivity to mitogens the Mycobacterial purified protein derivative (PPD) antigen was evaluated. Lymph node cells showed a proliferative response to ConA, PHA and PPD from rats with full-blown AA harvested at day 14 post-immunization. Lymphocytes from naïve, non-immunized rats had no significant proliferative response to PPD above medium control. However, lymphocytes from rats with AA had a strong proliferative response to mitogens at 3 days and also to PPD at 6 days, measured by $^3$H-thymidine incorporation. The effect of various concentrations of 2ME2 in vitro on this proliferative response was evaluated. Addition of 2ME2 to the culture on the day of initiation dose-dependently inhibited lymphocyte response to PPD, with an IC$_{50}$ of about 0.3 μg/mL. The 2ME2 also decreased the spontaneous proliferation in unstimulated cultures. A comparable inhibitory effect of 2ME2 in vitro on the proliferation induced by the mitogens was observed. There was no effect on viability since viability ($\geq$85% live cells) in all cultures was comparable. To further assess the effect of 2ME2 on lymphocyte responsiveness, lymph node cells harvested from rats treated with 2ME2 (30 mg/kg/d) from day 6-14 post-immunization were tested for proliferative response to PPD and the mitogens, Con A and PHA and compared to lymphocytes from vehicle-treated animals. DNA incorporation was increased by nearly five-fold in vehicle-treated rats. This response was significantly reduced with lymphocytes from rats that received 2ME2 treatment. In contrast, no difference in the proliferation induced by Con A or PHA was observed when the rats were treated with 2ME2 and cultures did not contain any added 2ME2. This suggests that 2ME2 had an immunomodulatory effect in vivo on antigen responsiveness.

We claim:

1. A method of treating rheumatic diseases comprising administering to a human or an animal an effective rheumatic arthritis-treating amount of
   a) a therapeutic agent having the structure

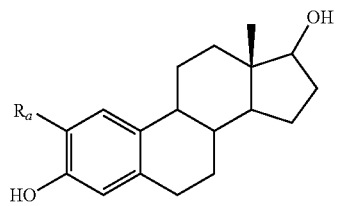

wherein $R_a$ is —$OCH_3$; and,
   b) a second compound being methotrexate;
wherein the first therapeutic agent and the second compound are administered in synergistic amounts for treating rheumatoid arthritis; and, wherein the synergistic amounts result in an inhibition of arthritic score that is greater than an expected inhibition of arthritic score.

2. The method of claim 1, wherein the therapeutic agent and the anti-rheumatic agent are administered in a single formulation.

3. The method of claim 1, wherein the therapeutic agent and the anti-rheumatic agent are administered in two or more separate formulations.

4. The method of claim 1, wherein said first therapeutic agent and said methotrexate are administered together.

5. The method of claim 1, wherein said first therapeutic agent and said methotrexate are administered separately.

6. The method of claim 1, wherein the first compound is administered in an amount of approximately 100 mg/kg of body weight and the second compound is administered in an amount of approximately 1 mg/kg of body weight.

7. A composition for treating rheumatic diseases comprising;
   a) a compound having the formula

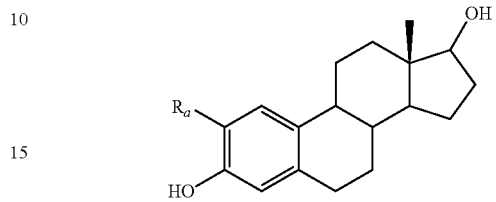

wherein $R_a$ is —$OCH_3$; and
   b) a second compound being methotrexate,
wherein the first and second compounds are provided in synergistic amounts effective for treating rheumatoid arthritis; and, wherein the synergistic amounts result in an inhibition of arthritic score that is greater than an expected inhibition of arthritic score.

8. The composition of claim 7, wherein the composition comprises:
   approximately 100 mg/kg of body weight of the first compound; and
   approximately 1 mg/kg of body weight of the second compound.

* * * * *